(12) United States Patent
Pitterna et al.

(10) Patent No.: US 7,732,416 B2
(45) Date of Patent: *Jun. 8, 2010

(54) AVERMECTINS SUBSTITUTED IN THE 4"-POSITION HAVING PESTICIDAL PROPERTIES

(75) Inventors: Thomas Pitterna, Basel (CH); Anthony Cornelius O'Sullivan, Basel (CH); William Lutz, Basel (CH)

(73) Assignee: Merial Limited, Duluth, GA (US)

(*) Notice: Subject to any disclaimer, the term of this patent is extended or adjusted under 35 U.S.C. 154(b) by 46 days.

This patent is subject to a terminal disclaimer.

(21) Appl. No.: 11/319,686

(22) Filed: Dec. 28, 2005

(65) Prior Publication Data

US 2006/0105970 A1 May 18, 2006

Related U.S. Application Data

(63) Continuation of application No. 10/468,684, filed as application No. PCT/EP02/02043 on Feb. 26, 2002, now abandoned.

(30) Foreign Application Priority Data

Feb. 27, 2001 (CH) .................................. 374/01

(51) Int. Cl.
*A61K 31/70* (2006.01)
*C07H 17/08* (2006.01)
(52) U.S. Cl. ........................ 514/30; 536/7.1
(58) Field of Classification Search .............. 514/27, 514/28, 30; 536/7.1
See application file for complete search history.

(56) References Cited

U.S. PATENT DOCUMENTS

| | | | |
|---|---|---|---|
| 4,203,976 A | 5/1980 | Fisher et al. | |
| 4,206,205 A | 6/1980 | Mrozik et al. | |
| 4,427,663 A | 1/1984 | Mrozik | |
| 4,622,313 A | 11/1986 | Wyvratt, Jr. et al. | |
| 4,831,016 A | 5/1989 | Mrozik et al. | |
| 4,895,837 A | 1/1990 | Mrozik et al. | |
| 5,023,241 A | 6/1991 | Linn et al. | |
| 5,057,499 A | 10/1991 | Mrozik et al. | |
| 5,169,839 A | 12/1992 | Linn et al. | |
| 5,192,546 A | 3/1993 | Abercrombie et al. | |
| 5,208,222 A | 5/1993 | Meinke et al. | |
| 5,229,415 A | 7/1993 | Linn et al. | |
| 5,346,698 A | 9/1994 | Abercrombie et al. | |
| 5,362,863 A | 11/1994 | Cvetovich | |
| 5,436,355 A | 7/1995 | Demchak | |
| 5,945,445 A | 8/1999 | Barringer et al. | |
| 5,981,500 A | 11/1999 | Bishop et al. | |
| 6,605,595 B1 | 8/2003 | Omura et al. | |
| 6,875,727 B2 | 4/2005 | Hofer et al. | |
| 6,933,260 B2 | 8/2005 | Piterna et al. | |
| 7,250,402 B2 | 7/2007 | Omura et al. | |
| 7,378,399 B2 | 5/2008 | Cassayre et al. | |

| | | | |
|---|---|---|---|
| 2006/0140997 A1 | 6/2006 | Pitterna et al. | |
| 2006/0205595 A1 | 9/2006 | Pitterna et al. | |
| 2008/0051353 A1 | 2/2008 | Jung et al. | |

FOREIGN PATENT DOCUMENTS

| | | |
|---|---|---|
| EP | 001688 | 5/1979 |
| EP | 0089202 | 9/1983 |
| EP | 0259688 | 3/1988 |
| EP | 0266131 | 5/1988 |
| EP | 0301806 | 1/1989 |
| EP | 0340849 | 11/1989 |
| EP | 0343708 | 11/1989 |
| EP | 0375393 | 6/1990 |
| EP | 0411897 | 6/1991 |
| EP | 0456509 | 11/1991 |

(Continued)

OTHER PUBLICATIONS

Mrozik, H. et al.: "4"-Deoxy-4"-Aminoavermectins with Potent Broad Spectrum Antiparasitic Activities", Bioogranic & Medicinal Chemistry Letters, vol. 5, No. 20, 1995, pp. 2435-2440.

(Continued)

*Primary Examiner*—Elli Peselev
(74) *Attorney, Agent, or Firm*—Judy Jarecki-Black; John Ezcurra; Merial Limited

(57) ABSTRACT

What is described are a compound of the formula (I)

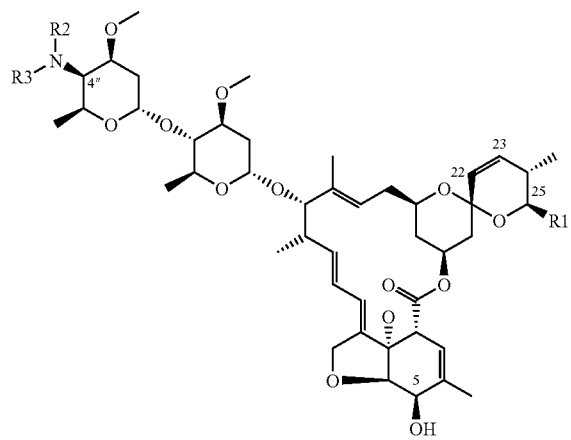

in which
$R_1$ is $C_1$-$C_{12}$alkyl, $C_3$-$C_8$cycloalkyl or $C_2$-$C_{12}$alkenyl;
$R_2$ is H, unsubstituted or mono- to pentasubstituted $C_1$-$C_{12}$alkyl or unsubstituted or mono- to pentasubstituted $C_1$-$C_{12}$alkenyl;
$R_3$ is $C_2$-$C_{12}$alkyl, mono- to pentasubstituted $C_1$-$C_{12}$alkyl, unsubstituted or mono- to pentasubstituted $C_1$-$C_6$alkoxy-$C_1$-$C_6$alkyl, unsubstituted or mono- to pentasubstituted $C_3$-$C_{12}$cycloalkyl, $C_2$-$C_{12}$alkenyl, $C_2$-$C_{12}$alkynyl; or
$R_2$ and $R_3$ together are an alkylene or alkenylene bridge;
with the proviso that $R_1$ is not sec-butyl or isopropyl if $R_2$ is H and $R_3$ is 2-hydroxyethyl, isopropyl, n-octyl or benzyl; or, if appropriate, in E/Z isomer, an E/Z isomer mixture and/or a tautomer thereof;

a process for preparing and using these compounds and their tautomers; pesticides whose active compound is selected from these compounds and their tautomers; and a process for preparing these compounds and compositions, and the use of these compounds and compositions.

11 Claims, No Drawings

FOREIGN PATENT DOCUMENTS

| | | |
|---|---|---|
| EP | 0465121 | 1/1992 |
| EP | 0506331 A | 9/1992 |
| EP | 0519731 | 12/1992 |
| EP | 1160252 A | 12/2001 |
| JP | 58 167591 | 10/1983 |
| WO | WO 93/15099 | 8/1993 |
| WO | WO9520877 | 8/1995 |
| WO | WO9622300 | 7/1996 |
| WO | WO 99 33343 | 7/1999 |
| WO | WO 02/068442 | 9/2002 |
| WO | WO 068441 | 9/2002 |
| WO | WO 03/20738 | 3/2003 |
| WO | WO 03/053988 A | 7/2003 |
| WO | WO 04/067534 | 8/2004 |

OTHER PUBLICATIONS

Wrzesinski, C.L. et al.: "Isolation and Identification of Residues of 4"-(EPI-Methylamino)-4"-Deoxyavermectin B1A Benzoate from the Surface of Cabbage," Journal of Agricultural and Food Chemistry, vol. 44, 1996, pp. 304-312.
U.S. Appl. No. 10/568,715, filed Feb. 17, 2006, Kasaba et al.
U.S. Appl. No. 10/560,390, filed Mar. 22, 2006, Pitterna et al.
U.S. Appl. No. 10/544,274, filed Aug. 3, 2005, Cassayre et al.
U.S. Appl. No. 10/544,281, filed Aug. 3, 2005, Quaranta et al.
U.S. Appl. No. 10/543,638, filed Jul. 28, 2005, Pitterna et al.
U.S. Appl. No. 10/543,643, filed Apr. 5, 2006, Pitternia et al.
U.S. Appl. No. 10/513,247, filed Nov. 2, 2004, Tobler et al.
U.S. Appl. No. 10/498,858, filed Jun. 14, 2004, Cassayre et al.
U.S. Appl. No. 10/488,225, filed Feb. 26, 2004, Tobler et al.
U.S. Appl. No. 11/319,687, filed Dec. 28, 2005, Pitterna et al.
U.S. Appl. No. 10/539,274, filed Mar. 9, 2006, Maienfisch et al.
Cvetovich et al., J. Org. Chem, 1994, 59, pp. 7704-7708.
Fisher, American Chemical Society Symposium, 1997, vol. 658, Phytochemicals for Pest Control.
J Med Chem 1992, 35, 3879-3884; "Affinity Probes for the Avermectin Bindig Proteins".
Jones, T K et al.; "Synthesis and Biological Activity of 4a,4-Disubstituted Avermectins"; Journal of Agriculture and Food Chemistry., American Chemical Society, 42 1994, p. 1786-1790.
Meinke et al. "Synthesis of Avermectin B1-4'-4'a -Oxide: A Precursor to Potent Antihelmintic Agents", Biorganic Medicinal Chemistry Letters, vol. 2, 1992 p. 537.
Mrozik, H et al. "Avermectin Acyl Derivatives with Anti Hempintic activity" Journal of Medicinal Chemistry, vol. 25, 1982, pp. 658-663.
Shoop et al; Efficacy in Sheep and Pharmacokinetics in Cattle that Led to the Selection of Epinomectin as a Topical Endetocide for Cattle, International Journal for Parasitology, 1996, 26 (11), 1227-35.
Yoshua et al.; Simultanious Determination of Residues of Emamectin and Its Metabolites, and Mibimectin, Ivermectin, and Abamectin in Crops by Liquid Chromatography with Fluorescence Detection. Journal of AOAC International vol. 84, No. 3 (910-917).

AVERMECTINS SUBSTITUTED IN THE 4''-POSITION HAVING PESTICIDAL PROPERTIES

This application is a continuation of U.S. Ser. No. 10/468,684, filed on Aug. 20, 2003 now abandoned, which is a National Phase filing under 35 U.S.C. §371 of International Application No. PCT/EP02/02043, filed on Feb. 26, 2002.

The invention provides (1) a compound of the formula

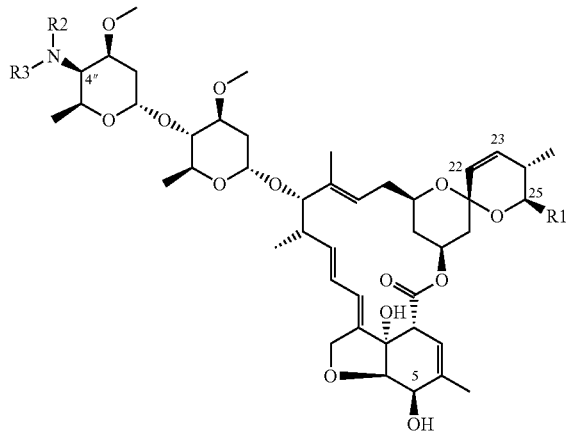

in which $R_1$ is $C_1$-$C_{12}$alkyl, $C_3$-$C_8$cycloalkyl or $C_2$-$C_{12}$alkenyl;

$R_2$ is H, unsubstituted or mono- to pentasubstituted $C_1$-$C_{12}$alkyl or unsubstituted or mono- to pentasubstituted $C_2$-$C_{12}$alkenyl;

$R_3$ is $C_2$-$C_{12}$alkyl, mono- to pentasubstituted $C_1$-$C_{12}$alkyl, unsubstituted or mono- to pentasubstituted $C_3$-$C_{12}$cycloalkyl, unsubstituted or mono- to pentasubstituted $C_1$-$C_6$alkoxy-$C_1$-$C_6$alkyl, unsubstituted or mono- to pentasubstituted $C_2$-$C_{12}$alkenyl, unsubstituted or mono- to pentasubstituted $C_2$-$C_{12}$alkynyl; or $R_2$ and $R_3$ together are a three- to seven-membered alkylene or a four- to seven-membered alkenylene bridge, in which a $CH_2$ group may be substituted by O, S or $NR_4$;

in which the substituents of the alkyl, alkoxyalkyl, alkenyl, alkynyl, alkylene, alkenylene and cycloalkyl radicals mentioned are selected from the group consisting of OH, halogen, halo-$C_1$-$C_2$alkyl, CN, SCN, $NO_2$, $C_2$-$C_6$alkynyl, $C_3$-$C_8$-cycloalkyl which is unsubstituted or substituted by one to three methyl groups; norbornylenyl, $C_3$-$C_8$cycloalkenyl which is unsubstituted or substituted by one to three methyl groups; $C_3$-$C_8$halocycloalkyl, $C_1$-$C_{12}$alkoxy, $C_3$-$C_8$cycloalkoxy, $C_1$-$C_{12}$alkylthio, $C_3$-$C_8$cycloalkylthio, $C_1$-$C_{12}$-haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, —$N(R_8)_2$, wherein the two $R_8$ are independent of each other; —C(=O)$R_5$, —O—C(=O)$R_6$, —NHC(=O)$R_5$, —S—C(=S)$R_6$, —P(=O)(O$C_1$-$C_6$alkyl)$_2$, —S(=O)$_2R_9$; —NH—S(=O)$_2R_9$, —OC(=O)—$C_1$-$C_6$alkyl-S(=O)$_2R_9$;

aryl, benzyl, heterocyclyl, aryloxy, benzyloxy, heterocyclyloxy, arylthio, benzylthio, heterocyclylthio; and also aryl, heterocyclyl, aryloxy, benzyloxy, heterocyclyloxy, arylthio, benzylthio or heterocyclylthio which, depending on the possibilities of substitution on the ring, are mono- to pentasubstituted by substituents selected from the group consisting of OH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl; methylenedioxy, —C(=O)$R_5$, —O—C(=O)—$R_6$, —NH—C(=O)$R_6$, —N(R_8)_2$, wherein the two $R_8$ are independent of each other; $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;

$R_4$ is H, $C_1$-$C_8$alkyl, hydroxy-$C_1$-$C_8$alkyl, $C_3$-$C_8$cycloalkyl, $C_2$-$C_8$alkenyl, $C_2$-$C_8$alkynyl, phenyl, benzyl —C(=O)$R_5$, or —$CH_2$—C(=O)—$R_5$;

$R_5$ is H, OH, SH, —$N(R_8)_2$, wherein the two $R_8$ are independent of each other; $C_1$-$C_{24}$alkyl, $C_2$-$C_{12}$alkenyl, $C_1$-$C_8$hydroxyalkyl, $C_1$-$C_{12}$haloalkyl, $C_1$-$C_{12}$alkoxy, $C_1$-$C_{12}$-haloakoxy, $C_1$-$C_6$alkoxy-$C_1$-$C_6$alkyl, $C_1$-$C_6$alkoxy-$C_1$-$C_6$alkoxy, $C_1$-$C_6$alkoxy-$C_1$-$C_6$alkoxy-$C_1$-$C_6$alkyl, $C_1$-$C_{12}$alkylthio, $C_2$-$C_8$alkenyloxy, $C_2$-$C_8$alkynyloxy, NH—$C_1$-$C_6$alkyl-C(=O)$R_7$, —N($C_1$-$C_6$alkyl)-$C_1$-$C_6$alkyl-C(=O)—$R_7$, —O—$C_1$-$C_2$alkyl-C(=O)$R_7$, —$C_1$-$C_6$alkyl-S(=O)$_2R_9$; aryl, benzyl, heterocyclyl, aryloxy, benzyloxy, heterocyclyloxy; or aryl, benzyl, heterocyclyl, aryloxy, benzyloxy or heterocyclyloxy, which are unsubstituted or mono- to trisubstituted in the ring independently of one another by halogen, nitro, $C_1$-$C_6$alkyl, $C_1$-$C_6$alkoxy, $C_1$-$C_6$haloalkyl or $C_1$-$C_6$haloalkoxy;

$R_6$ is H, $C_1$-$C_{24}$alkyl, $C_1$-$C_{12}$haloalkyl, $C_1$-$C_{12}$hydroxyalkyl, $C_2$-$C_8$alkenyl, $C_2$-$C_8$alkynyl, $C_1$-$C_6$alkoxy-$C_1$-$C_6$alkyl, $(NR_8)_2$, wherein the two $R_8$ are independent of each other; —$C_1$-$C_6$alkyl-C(=O)$R_8$, —$C_1$-$C_6$alkyl-S(=O)$_2R_9$, aryl, benzyl, heterocyclyl; or aryl, benzyl or heterocyclyl which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

$R_7$ is H, OH, $C_1$-$C_{24}$alkyl which is optionally substituted with OH, or —S(=O)$_2$—$C_1$-$C_6$alkyl; $C_1$-$C_{12}$alkenyl, $C_1$-$C_{12}$alkynyl, $C_1$-$C_{12}$alkoxy, $C_1$-$C_6$alkoxy-$C_1$-$C_6$alkyl, $C_1$-$C_6$alkoxy-$C_1$-$C_6$alkoxy, $C_2$-$C_8$alkenyloxy, aryl, aryloxy, benzyloxy, heterocyclyl, heterocyclyloxy or —$N(R_8)_2$, wherein the two $R_8$ are independent of each other;

$R_8$ H, $C_1$-$C_6$alkyl, which is optionally substituted with one to five substituents selected from the group consisting of halogen, $C_1$-$C_6$alkoxy, hydroxy and cyano; $C_1$-$C_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

$R_9$ is H, $C_1$-$C_6$alkyl, which is optionally substituted with one to five substituents selected from the group consisting of halogen, $C_1$-$C_6$alkoxy, hydroxy and cyano; aryl, benzyl, hetero-aryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

with the proviso that $R_1$ is not sec-butyl or isopropyl if $R_2$ is H and $R_3$ is 2-hydroxyethyl, isopropyl, n-octyl or benzyl;

or, if appropriate, an E/Z isomer, E/Z isomer mixture and/or tautomer thereof;

a process for preparing these compounds, their isomers and tautomers and the use of these compounds, their isomers and tautomers; pesticides whose active compound is selected from these compounds and their tautomers; and a method for controlling pests using these compositions.

The literature proposes certain macrolide compounds for controlling pests. However, the biological properties of these known compounds are not entirely satisfactory, and, as a consequence, there is still a need for providing further compounds having pesticidal properties, in particular for the control of insects and representatives of the order Acarina. According to the invention, this object is achieved by providing the present compounds of the formula (I).

The compounds claimed according to the invention are derivatives of Avermectin. Avermectins are known to the person skilled in the art. They are a group of structurally closely related pesticidally active compounds which are obtained by fermenting a strain of the microorganism *Streptomyces avermitilis*. Derivatives of Avermectins can be obtained by conventional chemical syntheses.

The Avermectins which can be obtained from *Streptomyces avermitilis* are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent $R_1$ (in position 25) is a sec-butyl radical and an isopropyl radical, respectively. The number 1 in the name of the compounds means that atoms 22 and 23 are linked by double bonds; the number 2 means that they are linked by a single bond and that the C atom 23 carries an OH group. The above nomenclature is adhered to in the description of the present invention to denote the specific structure type in the not naturally occurring Avermectin derivatives according to the invention which corresponds to the naturally occurring Avermectin. What is claimed according to the invention are derivatives of compounds of the B1 series, in particular mixtures of derivatives of Avermectin B1a and Avermectin B1b.

Some of the compounds of the formula (I) can be present as tautomers. Accordingly, hereinabove and hereinbelow, the compounds of the formula (I) are, if appropriate, also to be understood as including the corresponding tautomers, even if the latter are not specifically mentioned in each case.

Unless defined otherwise, the general terms used hereinabove and hereinbelow have the meanings given below.

Unless defined otherwise, carbon-containing groups and compounds containing in each case 1 up to and including 6, preferably 1 up to and including 4, in particular 1 or 2, carbon atoms.

Halogen—as a group per se and also as a structural element of other groups and compounds, such as haloalkyl, haloalkoxy and haloalkylthio—is fluorine, chlorine, bromine or iodine, in particular fluorine, chlorine or bromine, especially fluorine or chlorine.

Alkyl—as a group per se and also as a structural element of other groups and compounds, such as haloalkyl, alkoxy and alkylthio—is, in each case taking into account the number of carbon atoms contained in each case in the group or compound in question, either straight-chain, i.e. methyl, ethyl, propyl, butyl, pentyl, hexyl, heptyl or octyl, or branched, for example isopropyl, isobutyl, sec-butyl, tert-butyl, isopentyl, neopentyl or isohexyl.

Cycloalkyl—as a group per se and also as a structural element of other groups and compounds, such as, for example, of halocycloalkyl, cycloalkoxy and cycloalkylthio—is, in each case taking into account the number of carbon atoms contained in each case in the group or compound in question, cyclopropyl, cyclobutyl, cyclopentyl, cyclohexyl, cycloheptyl or cyclooctyl.

Alkenyl—as a group per se and also as a structural element of other groups and compounds—is, taking into account the number of carbon atoms and conjugated or isolated double bonds contained in the group, either straight-chain, for example vinyl, allyl, 2-butenyl, 3-pentenyl, 1-hexenyl, 1-heptenyl, 1,3-hexadienyl or 1,3-octadienyl, or branched, for example isopropenyl, isobutenyl, isoprenyl, tert-pentenyl, isohexenyl, isoheptenyl or isooctenyl. Preference is given to alkenyl groups having 3 to 12, in particular 3 to 6, especially 3 or 4, carbon atoms.

Alkynyl—as a group per se and also as a structural element of other groups and compounds—is, in each case taking into account the number of carbon atoms and conjugated or isolated double bonds contained in the group or compound in question, either straight-chain, for example ethynyl, propargyl, 2-butynyl, 3-pentynyl, 1-hexynyl, 1-heptynyl, 3-hexen-1-ynyl or 1,5-heptadien-3-ynyl, or branched, for example 3-methylbut-1-ynyl, 4-ethylpent-1-ynyl, 4-methylhex-2-ynyl or 2-methylhept-3-ynyl. Preference is given to alkynyl groups having 3 to 12, in particular 3 to 6, especially 3 or 4, carbon atoms.

Alkylene and alkenylene are straight-chain or branched bridge members; they are in particular —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2(CH_3)CH_2$—$CH_2$—, —$CH_2C(CH_3)_2$—$CH_2$—, —$CH_2$—CH=CH—$CH_2$ or —$CH_2$—CH=CH—$CH_2$—$CH_2$—.

Halogen-substituted carbon-containing groups and compounds, such as, for example, halogen-substituted alkyl, alkenyl, alkynyl, cycloalkyl, alkoxy or alkylthio, can be partially halogenated or perhalogenated, where in the case of polyhalogenation the halogen substituents can be identical or different. Examples of haloalkyl—as a group per se and also as a structural element of other groups and compounds, such as haloalkoxy or haloalkylthio—are methyl which is mono- to trisubstituted by fluorine, chlorine and/or bromine, such as $CHF_2$ or $CF_3$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl which is mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers, mono- to undecasubstituted by fluorine, chlorine and/or bromine, such as $CF(CF_3)(CHF_2)CF_3$ or $CH_2(CF_2)_3CF_3$; and hexyl or one of its isomers, mono- to tridecasubstituted by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is in particular phenyl, naphthyl, anthracenyl, phenanthrenyl, perylenyl or fluorenyl, preferably phenyl.

Heterocyclyl is understood as being a three- to seven-membered monocyclic ring, which may be saturated or unsaturated, and that contains from one to three hetero atoms selected from the group consisting of N, O and S, especially N and S; or a bicyclic ring-system having from 8 to 14 ring atoms, which may be saturated or unsaturated, and that may contain either in only one ring or in both rings independently of one another, one or two hetero atoms selected from N, O and S.

Heterocyclyl is in particular piperidinyl, piperazinyl, oxiranyl, morpholinyl, thiomorpholinyl, pyridyl, N-oxidopyridinio, pyrimidyl, pyrazinyl, s-triazinyl, 1,2,4-triazinyl, thienyl, furanyl, dihydrofuranyl, tetrahydrofuranyl, pyranyl, tetrahydropyranyl, pyrrolyl, pyrrolinyl, pyrrolidinyl, pyrazolyl, imidazolyl, imidazolinyl, thiazolyl, isothiazolyl, triazolyl, oxazolyl, thiadiazolyl, thiazolinyl, thiazolidinyl, oxadiazolyl, phthalimidoyl, benzothienyl, quinolinyl, quinoxalinyl, benzofuranyl, benzimidazolyl, benzpyrrolyl, benzthiazolyl, indolinyl, isoindolinyl, cumarinyl, indazolyl, benzothiophenyl, benzofuranyl, pteridinyl or purinyl, which are preferably attached via a C atom; thienyl, benzofuranyl, benzothiazolyl, tetrahydropyranyl or indolyl is preferred; in particular pyridyl or thiazolyl. The said heterocyclyl radicals may preferably be unsubstituted or—depending on the substitution possibilities on the ring system—substituted by 1 to 3 substituents selected from the group consisting of halogen, =O, —OH, =S, SH, nitro, $C_1$-$C_6$alkyl, $C_1$-$C_6$hydroxyalkyl, $C_1$-$C_6$alkoxy, $C_1$-$C_6$haloalkyl, $C_1$-$C_6$haloalkoxy, phenyl, benzyl, —C(=O)—$R_6$ and —$CH_2$—C(=O)—$R_6$.

In the context of the present invention, preference is given to (2) compounds according to group (1) of the formula (I) in which $R_1$ is isopropyl or sec-butyl, preferably to those in which a mixture of the isopropyl and the sec-butyl derivative is present;

(3) compounds according to group (2) of the formula (I), in which $R_2$ is H;

(4) compounds according to group (2) of the formula (I) in which $R_2$ is $C_1$-$C_8$alkyl, in particular methyl;

(5) compounds according to group (2) of the formula (I) in which $R_2$ is ethyl;

(6) compounds according to group (2) of the formula (I) in which $R_2$ is n-propyl;

(7) compounds according to any of groups (1) to (6) of the formula (I) in which $R_3$ is unsubstituted or substituted, in particular unsubstituted, $C_2$-$C_5$ alkyl;

(8) compounds according to any of groups (1) to (7) of the formula (I) in which $R_3$ is ethyl;

(9) compounds according to any of groups (1) to (7) of the formula (I) in which $R_3$ is n-propyl;

(10) compounds according to any of groups (2) to (7) of the formula (I) in which $R_3$ is isopropyl;

(11) compounds according to any of groups (1) to (7) of the formula (I) in which $R_3$ is n-butyl, sec-butyl, isobutyl or tert-butyl;

(12) compounds according to any of groups (1) to (6) of the formula (I) in which $R_3$ is unsubstituted or substituted, in particular unsubstituted, $C_6$-$C_{12}$alkyl;

(13) compounds according to any of groups (1) or (2) of the formula (I) in which $R_2$ and $R_3$ together are —$CH_2$—$CH_2$—$CH_2$— or —$CH_2$—$CH_2$—$CH_2$—$CH_2$—;

(14) compounds according to any of groups (1) or (2) of the formula (1) in which $R_2$ and $R_3$ together are —$CH_2$—$CH_2$—O—$CH_2$—$CH_2$— or —$CH_2$—$CH_2$—N($CH_3$)—$CH_2$—$CH_2$—;

(15) compounds according to any of groups (1) to (6) of the formula (I) in which $R_3$ is substituted $C_1$-$C_4$alkyl and the substituents are selected from the group consisting of OH, halogen, $C_3$-$C_8$cycloalkyl, $C_3$-$C_8$cycloalkenyl which is unsubstituted or substituted by one to three methyl groups, $C_1$-$C_{12}$alkoxy, $C_2$-$C_8$alkynyl, —C(=O)$R_5$, —NHC(=O)$R_6$, —P(=O)(O$C_1$-$C_6$alkyl)$_2$; phenyl, naphthyl, anthracenyl, phenanthrenyl, fluorenyl, perylenyl or heterocyclyl which are unsubstituted or, depending on the possibility of substitution on the ring, mono- to pentasubstituted;

and in particular to those in which the substituents of $R_3$ are selected from the group consisting of halogen, $C_3$-$C_8$cycloalkyl, $C_2$-$C_8$alkynyl, —C(=O)$R_5$, —NHC(=O)$R_6$, —P(=O)(O$C_1$-$C_6$alkyl)$_2$; phenyl, naphthyl, anthracenyl, pyridyl, thiazolyl, imidazolyl, furanyl, quinolinyl, pyrazolyl, which are unsubstituted or, depending on the possibility of substitution on the ring, mono- to trisubstituted;

(16) compounds according to any of groups (1) to (6) of the formula (I) in which $R_3$ is benzyl which carries, on the aromatic moiety, one to three substituents selected from the group consisting of OH, halogen, CN, $NO_2$, $C_1$-$C_2$alkyl, dimethylamino-$C_1$-$C_4$alkoxy, $C_3$-$C_6$cycloalkyl, $C_1$-$C_2$haloalkyl, $C_1$-$C_2$alkoxy, $C_1$-$C_2$haloalkoxy, phenoxy, phenyl-$C_1$-$C_6$alkyl, phenyl-$C_1$-$C_4$alkenyl, unsubstituted or chlorine- or methoxy-substituted phenoxy, unsubstituted or chlorine-, methoxy- or trichloromethyl-substituted benzyloxy, methylenedioxy, —C(=O)$R_5$, —O—C(=O)$R_6$ and NHC(=O)$R_6$;

$R_5$ is H, OH, $NH_2$, NH($C_1$-$C_2$alkyl), N($C_1$-$C_2$alkyl)$_2$, —O—$C_1$-$C_2$alkyl-C(=O)—$R_7$, —NH$C_1$-$C_2$alkyl-C(=O)—$R_7$, $C_1$-$C_6$alkyl, $C_1$-$C_2$alkoxy, $C_1$-$C_2$alkoxy-$C_1$-$C_2$alkoxy, $C_2$-$C_4$alkenyloxy, $C_2$-$C_4$alkynyloxy; phenyl, phenoxy, benzyloxy, NH-phenyl, NH—$C_1$-$C_6$alkyl-C(=O)-$R_7$; or phenyl, phenoxy, benzyloxy, NH-phenyl which are substituted by halogen, nitro, methoxy, trifluoromethyl or trifluoromethoxy;

$R_6$ is H, $C_1$-$C_3$alkyl, phenyl or benzyl; and $R_7$ is H, OH, $NH_2$, NH($C_1$-$C_{12}$alkyl), N($C_1$-$C_{12}$alkyl)$_2$, $C_1$-$C_{12}$alkyl, $C_1$-$C_{12}$alkoxy, $C_1$-$C_6$alkoxy-$C_1$-$C_6$alkoxy, $C_2$-$C_8$alkenyloxyl, phenyl, phenoxy, benzyloxy or NH-phenyl;

(17) compounds according to any of groups (1) to (6) of the formula (I) in which $R_3$ is $C_1$-$C_4$alkyl-C(=O)$R_5$, in particular —$CH_2$—C(=O)$R_5$; and $R_5$ is H, OH, $NH_2$, NH($C_1$-$C_2$alkyl), N($C_1$-$C_2$alkyl)$_2$, $C_1$-$C_4$alkyl, $C_1$-$C_1$-$C_{12}$alkoxy, $C_2$-$C_4$alkenyloxy, phenyl, phenoxy, benzyloxy, NH-phenyl, NH—$C_1$-$C_2$alkyl-C(=O)—O—$C_1$-$C_2$alkylphenyl, —P(=O)(O$C_1$-$C_6$alkyl); or phenyl, phenoxy, benzyloxy or NH-phenyl which are substituted by chlorine, fluorine, methoxy, trifluoromethyl or trifluoromethoxy;

very particularly those in which $R_5$ is $C_1$-$C_{12}$alkoxy;

(18) compounds according to any of groups (1) to (6) of the formula (I) in which $R_3$ is $C_2$-$C_6$alkyl-NHC(=O)$R_6$ and $R_6$ is H, $C_1$-$C_4$alkyl, $C_2$-$C_4$alkenyl, $C_2$-$C_4$alkynyl, phenyl or benzyl;

(19) compounds according to any of groups (1) to (6) of the formula (I) in which $R_3$ is —$CH_2$-heterocyclyl;

especially wherein heterocyclyl is pyridyl, furanyl, tetrahydrofuranyl, pyranyl, tetrahydropyranyl, pyrazolyl, imidazolyl, thiazolyl, benzothienyl, quinolinyl, quinoxalinyl, benzofuranyl, benzimidazolyl, benzpyrrolyl, benzothiazolyl, indolyl, cumarinyl or indazolyl, where the radicals mentioned are unsubstituted or mono- or disubstituted independently of one another by halogen, trifluoromethyl, trifluoromethoxy or nitro; particularly preferably pyridyl, furanyl, pyrazolyl, imidazolyl, thiazolyl, benzimidazolyl, benzopyrrolyl, benzothiazolyl or indolyl which are unsubstituted or mono- or disubstituted independently of one another by halogen, trifluoromethyl, trifluoromethoxy or nitro; in particular pyridyl or thiazolyl which are unsubstituted or mono- or disubstituted independently of one another by halogen, trifluoromethyl, trifluoromethoxy or nitro, in particular monosubstituted by chlorine;

(20) compounds according to any of groups (1) to (6) of the formula (I) in which $R_3$ is $C_2$-$C_{10}$alkenyl, in particular $C_2$-$C_4$alkenyl, which is unsubstituted or mono- or disubstituted, in particular monosubstituted, by $C_2$-$C_4$alkynyl, —C(=O)—C$_1$-C$_4$alkoxy, —C(=O)—C$_1$-C$_4$alkyl-benzoyl, phenyl or halogen; in particular those in which R$_3$ is —CH$_2$—CH=CH$_2$;

(21) compounds according to any of groups (1) to (6) of the formula (I) in which R$_3$ is branched unsubstituted C$_4$-C$_{10}$alkyl;

(22) compounds according to any of groups (1) to (6) of the formula (I) in which R$_3$ is branched substituted C$_3$-C$_{10}$alkyl;

(23) compounds according to any of groups (1) to (6) of the formula (I) in which R$_3$ is unsubstituted benzyl;

(24) compounds according to any of groups (1) to (6) of the formula (I) in which R$_3$ is —CH$_2$—CH$_2$—CN, CH$_2$—CH$_2$—CO—C$_1$-C$_4$alkyl, —CH$_2$—CH$_2$—CO-phenyl or CH$_2$—CH$_2$—CO—C$_1$-C$_4$alkoxy; especially —CH$_2$—CH$_2$—CN or —CH$_2$—CH$_2$—CO—C$_1$-C$_4$alkoxy; particularly CH$_2$—CH$_2$—CN;

(25) compounds according to any of groups (1) to (6) of the formula (I) in which R$_3$ is —CH$_2$—CH$_2$—CH$_2$—O—CO—C$_1$-C$_4$alkyl, —CH$_2$—CH$_2$—CH$_2$—O—CO-Aryl, CH$_2$—CH$_2$—CH$_2$—CO—C$_1$-C$_4$alkoxy, —CH$_2$—CH$_2$—CO-subst-C$_1$-C$_4$alkyl, —CH$_2$—CH$_2$—CO-substituted-Aryl, —CH$_2$—CH$_2$—CO-subst.Alkoxy; especially —CH$_2$—CH$_2$—CH$_2$—O—CO-Alkyl or CH$_2$—CH$_2$—CH$_2$—O—CO-Aryl; particularly —CH$_2$—CH$_2$—CH$_2$—O—CO—C$_1$-C$_4$alkyl or —CH$_2$—CH$_2$—CH$_2$—O—CO-phenyl; very especially —CH$_2$—CH$_2$—CH$_2$—O—CO-methyl;

(26) compounds according to any of groups (1) to (6) of the formula (I) in which the radical R$_3$ is substituted with —NHC(=O)R$_5$, especially wherein R$_3$ is —(CH$_2$)$_3$—NHC(=O)R$_5$;

(27) compounds according to any of groups (1) to (6) of the formula (I) in which the radical R$_3$ is substituted with —S—C(=S)R$_6$, especially wherein R$_3$ is —(CH$_2$)$_3$—S—C(=S)R$_6$;

(28) compounds according to any of groups (1) to (6) of the formula (I) in which the radical R$_3$ is substituted with —NH—S(=O)$_2$R$_9$, especially wherein R$_3$ is —(CH$_2$)$_3$—NH—S(=O)$_2$R$_9$;

(29) compounds according to any of groups (1) to (6) of the formula (I) in which the radical R$_3$ is substituted with —OC(=O)—C$_1$-C$_6$alkyl-S(=O)$_2$R$_9$; especially wherein R$_3$ is —(CH$_2$)$_3$—OC(=O)—C$_1$-C$_6$alkyl-S(=O)$_2$R$_9$;

(30) compounds according to any of groups (1) to (6) of the formula (I) in which R$_3$ is monosubstituted C$_1$-C$_6$alkoxy-C$_1$-C$_6$alkyl;

(31) In the context of the invention, particular preference is given to the compounds of the formula (I) listed in the tables and, if appropriate, to their E/Z isomers and E/Z isomer mixtures; these are in particular the compounds 4"-deoxy-4"-epi-N-ethylaminoavermectin B1;
4"-deoxy-4"-epi-N-prop-1-ylaminoavermectin B1;
4"-deoxy-4"-epi-(N-ethyl-N-methylamino)avermectin B1;
4"-deoxy-4"-epi-(N-methyl-N-prop-1-ylamino)avermectin B1;
4"-deoxy-4"-epi-(N-isopropyl-N-methylamino)avermectin B1;
4"-deoxy-4"-epi-(N-methyl-N-1-propen-3-ylamino)avermectin B1;
4"-deoxy-4"-epi-(N-methyl-N-ethoxycarbonylmethylamino)avermectin B1;
4"-deoxy-4"-epi-(N-methyl-N-benzylamino)avermectin B1;
4"-deoxy-4"-epi-(N-methyl-N-4-difluoromethoxyphenylmethylamino)avermectin B1;
4"-deoxy-4"-epi-(N-methyl-N-2,5-dichlorophenylamino)avermectin B1;
4"-deoxy-4"-epi-(N-methyl-N-2,5-difluorophenylmethylamino)avermectin B1;
4"-deoxy-4"-epi-(N-methyl-N-2,3,4-trifluorophenylmethylamino)avermectin B1;
4"-deoxy-4"-epi-(pyrrolidin-1-yl)avermectin B1;
4"-deoxy-4"-epi-(azetidin-1-yl)avermectin B1;
4"-Desoxy-4"-epi-[N-(2-hydroxy-2-methyl-propyl)-N-methylamino]-avermectin B1;
4"-Desoxy-4"-epi-[N-(3-acetoxy-propyl)-N-methylamino]-avermectin B1;
4"-Desoxy-4"-epi-N-(2-cyano-ethylamino)-avermectin B1;
4"-Desoxy-4"-epi-N-[(6-chloro-pyridin-3-ylmethyl)-amino]-avermectin B1; and
4"-deoxy-4"-epi-(N-methyl-N-[3-{2-oxo-2-phenylethoxycarbonyl}allyl]amino)avermectin B1.

The invention also provides a process for preparing the compounds of the formula (I) and, if appropriate, tautomers thereof, wherein (A) to prepare a compound of the formula (I) in which R$_1$ has the same meanings as given above under (1) for formula (I), R$_2$ is hydrogen and R$_3$ is a group R$_{31}$—CH—R$_{32}$ in which R$_{31}$ is C$_1$-C$_6$alkyl, phenyl, heterocyclyl or substituted C$_1$-C$_6$alkyl, phenyl or heterocycylyl and R$_{32}$ is H or unsubstituted or substituted C$_1$-C$_5$alkyl;

a compound of the formula (I) in which R$_1$ has the same meanings as given above under (1) for formula (I) and R$_2$ and R$_3$ are hydrogen and which is known and can be prepared by known methods is reacted in the presence of a reducing agent with a compound R$_{31}$—C(=O)R$_{32}$ in which R$_3$, and R$_{32}$ have the same meanings as given above; or (B) to prepare a compound of the formula (Ia) in which R$_1$ and R$_2$ have the same meanings as given above under (1) for formula (I) and R$_3$ has the same meanings as given above under (1) for formula (I), except for hydrogen, a compound of the formula (Ia) in which R$_1$ and R$_2$ have the same meanings as given above under (1) for formula (I) and R$_3$ is hydrogen and which can be prepared by methods known per se;

is reacted with a compound of the formula R$_3$-Hal in which R$_3$ has the same meanings as given above under (I) for the formula (I) and Hal is halogen, in particular bromine or iodine; or (C) to prepare a compound of the formula (I) in which R$_1$ and R$_2$ have the same meanings as given above under (1) for formula (I) and R$_3$ is hydroxyl-substituted —CH$_2$—C$_1$-C$_{11}$alkyl, a compound of the formula (I) in which R$_1$ and R$_2$ have the same meanings as given above under (1) for formula (I), R$_3$ is —C(=O)—R$_5$-substituted C$_1$-C$_{11}$alkyl and R$_5$ is OH or alkoxy is reacted with a reducing agent; or (D) to prepare a compound of the formula (I) in which R$_1$ and R$_2$ have the same meanings as given above under (1) for formula (I) and R$_3$ is COOH-substituted C$_1$-C$_{12}$alkyl, a compound of the formula (I) in which R$_1$ and R$_2$ have the same meanings as given above under (1) for formula (I), R$_3$ is —C(=O)—R$_5$-substituted C$_1$-C$_{12}$alkyl and R$_5$ is C$_1$-C$_6$alkoxy or benzyloxy is reacted with a base or a reducing agent; or (E) to prepare a compound of the compound (I) in which R$_1$ and R$_3$ have the same meanings as given above under (1) for formula (I) and R$_2$ is methyl, a compound of the formula (I) in which R$_1$ and R$_3$ have the same meanings as given above under (1) for formula (I) and R$_2$ is hydrogen is reacted with a compound of the formula methyl-Hal in which Hal is a halogen, in particular bromine or iodine; or with formaldehyde in the presence of a reducing agent; or (F) to prepare a compound of the formula (I) in which $R_1$ and $R_2$ have the same meanings as given above under (1) for formula (I) and $R_3$ is —C(=O)N($R_{10}$)$_2$-substituted $C_1$-$C_{12}$alkyl and in which the two $R_{10}$ independently of one another are H or unsubstituted or substituted $C_1$-$C_{12}$alkyl, a compound of the formula (I) in which $R_1$ and $R_2$ have the same meanings as given above under (1) for formula (I), $R_3$ is —C(=O)$R_5$-substituted $C_1$-$C_{12}$alkyl and $R_5$ is OH is reacted with a compound of the formula NH($R_{10}$)$_2$ in which $R_{10}$ is H or unsubstituted or substituted $C_1$-$C_{12}$alkyl in the presence of a dehydrating agent; or (G) to prepare a compound of the formula (I) in which $R_1$ and $R_2$ have the same meanings as given above under (1) for formula (I) and $R_3$ is hydroxyl-substituted $C_4$-$C_{12}$ alkyl a compound of the formula (I) in which $R_1$ and $R_2$ have the same meanings as given above under (1) for formula (I), $R_3$ is —C(=O)—$R_5$-substituted $C_1$-$C_5$alkyl and $R_5$ is $C_1$-$C_{12}$alkoxy is reacted with two moles of a $C_1$-$C_3$alkylmagnesium halide or $C_1$-$C_3$alkyllithium reagent; or (H) to prepare a compound of the formula (I) in which $R_1$ has the same meanings as given above under (1) for formula (I) and $R_2$ and $R_3$ together are a three- to seven-membered alkylene or a four- to seven-membered alkenylene bridge in which one CH$_2$ group may be replaced by O, S or NR$_4$ and $R_4$ has the same meanings as given above under (1) for formula (I);

a compound of the formula (I) in which $R_1$ has the same meanings as given above under (1) for formula (I) and $R_2$ and $R_3$ are hydrogen is reacted with a compound of the formula Hal-($C_3$-$C_7$alkylene)-Hal or Hal-($C_4$-$C_7$alkenylene)-Hal in which Hal is a halogen, in particular bromine or iodine, and in which one CH$_2$ group may be replaced by O, S or NR$_4$, and in which $R_4$ has the same meanings as given above under (1) for formula (I); or (I) to prepare a compound of the formula (I) in which $R_1$ has the same meanings as given above under (1) for formula (I) and $R_2$ and $R_3$ are identical and have the same meanings as given above under (1) for formula (I), a compound of the formula (I) in which $R_1$ has the same meanings as given above under (1) for formula (I) and $R_2$ and $R_3$ are hydrogen is reacted with two moles of a compound of the formula $R_3$-Hal in which $R_3$ has the same meanings as given above for the formula (I) and Hal is halogen, in particular bromine or iodine; or (J) to prepare a compound of the formula (I) in which $R_2$ and $R_3$ are identical and are unsubstituted or mono- to pentasubstituted —CH$_2$—$C_1$-$C_{11}$alkyl, unsubstituted or mono- to pentasubstituted —CH$_2$—$C_1$-$C_{11}$alkenyl or unsubstituted or mono- to pentasubstituted —CH$_2$—$C_1$-$C_{11}$alkynyl, a compound of the formula (I) in which $R_1$ has the same meanings as given above under (1) for formula (I) and $R_2$ and $R_3$ are hydrogen is reacted with two moles of a compound of the formula $R_{31}$—CHO in which $R_{31}$ is unsubstituted or mono- to penta-substituted $C_1$-$C_{11}$alkyl, unsubstituted or mono- to pentasubstituted $C_1$-$C_{11}$alkenyl or unsubstituted or mono- to pentasubstituted $C_1$-$C_{11}$alkynyl in the presence of a reducing agent.

The comments made above in connection with tautomers of compounds of formula (I) apply analogously to the starting materials mentioned hereinabove and hereinbelow in respect of their tautomers.

The reactions described hereinabove and hereinbelow are carried out in a manner known per se, for example in the absence or, customarily, in the presence of a suitable solvent or diluent or of a mixture thereof, the reactions being carried out, as required, with cooling, at room temperature or with heating, for example in a temperature range of approximately from −80° C. to the boiling temperature of the reaction medium, preferably from approximately 0° C. to approximately +150° C., and, if necessary, in a closed vessel, under pressure, under an inert gas atmosphere and/or under anhydrous conditions. Especially advantageous reaction conditions can be found in the Examples.

The reaction time is not critical; a reaction time of from about 0.1 to about 24 hours, especially from about 0.5 to about 10 hours, is preferred.

The product is isolated by customary methods, for example by means of filtration, crystallisation, distillation or chromatography, or any suitable combination of such methods.

The starting materials mentioned hereinabove and hereinbelow that are used for the preparation of the compounds of formula (I) and, where applicable, their tautomers are known or can be prepared by methods known per se, e.g. as indicated below.

Process Variant (A):

Examples of solvents and diluents include: aromatic, aliphatic and alicyclic hydrocarbons and halogenated hydrocarbons, such as benzene, toluene, xylene, mesitylene, Tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether; ethylene glycol monomethyl ether, ethylene glycol monoethyl ether, ethylene glycol dimethyl ether, dimethoxydiethyl ether, tetrahydrofuran or dioxane; alcohols, such as methanol, ethanol, propanol, isopropanol, butanol, ethylene glycol or glycerol; carboxylic acid, such as acetic acid or formic acid; amides, such as N,N-dimethylformamide, N,N-diethylformamide, N,N-dimethylacetamide, N-methyl-pyrrolidone or hexamethylphosphoric acid triamide; nitriles, such as acetonitrile or propionitrile; and sulfoxides, such as dimethyl sulfoxide; and also water; or mixtures of the mentioned solvents;

especially suitable are ethers, alcohols, water and carboxylic acids, more especially tetrahydrofuran, acetic acid or water.

The reactions are advantageously carried out in a temperature range of from about room temperature to the boiling point of the solvent used; preference being given to reaction at 10 to 30° C.

In a preferred embodiment of Variant (A) the reaction is carried out at room temperature, in tetrahydrofuran in the presence of acetic acid. Especially preferred conditions for the reaction are described in Example P1.1.

Process Variant (B):

Examples of solvents and diluents include: aromatic, aliphatic and alicyclic hydrocarbons and halogenated hydrocarbons and ethers as listed above under Process variant (A); ketones, such as acetone, methyl ethyl ketone or methyl isobutyl ketone; alcohols, such as methanol, ethanol, propanol, isopropanol, butanol, ethylene glycol or glycerol; carboxylic acid esters, such as methyl acetate, ethyl acetate, or esters of benzoic acid; amides as listed above under Process variant (A); nitriles, such as acetonitrile or propionitrile; and sulfoxides, such as dimethyl sulfoxide; and also water; or mixtures of the mentioned solvents;

especially suitable are water, esters of organic acids, halogenated hydrocarbons and aromatic hydrocarbons; more especially two-phase mixtures of such an organic solvent with water.

The reactions are advantageously carried out in a temperature range of approximately from room temperature to the boiling point of the solvent used, preferably from room temperature up to 90° C., especially up to 60° C., and in the presence of a base, preferably an inorganic base, for example sodium hydroxide, potassium hydroxide, sodium carbonate or sodium hydrogen carbonate.

Especially preferred conditions for the reaction are described, for example, in Examples P1.2, P1.3, P2.1 and P2.7.

Process Variant (C):

Examples of solvents and diluents include: aromatic, aliphatic and alicyclic hydrocarbons and halogenated hydrocarbons and ethers, amides and nitriles as listed above under Process variant (A); and sulfoxides, such as dimethyl sulfoxide; or mixtures of the mentioned solvents; ethers and hydrocarbons being especially suitable.

The reactions are advantageously carried out in a temperature range of from 0° C. to the boiling point of the solvent used, preferably from 0° C. to room temperature. Especially preferred conditions for the reaction are described, for example, in Example P2.2.

Process Variant (D):

Suitable solvents include those mentioned under Variant (A); additionally also ketones, such as acetone, methyl ethyl ketone and methyl isobutyl ketone; and carboxylic acids, such as acetic acid or formic acid; carboxylic acid esters, such as methyl acetate, ethyl acetate, or esters of benzoic acid.

The reactions are advantageously carried out in a temperature range of approximately from room temperature to the boiling point of the solvent used, preferably in the presence of an inorganic base, for example lithium hydroxide, sodium hydroxide, potassium hydroxide, sodium carbonate or sodium hydrogen carbonate.

Especially preferred conditions for this Process variant are described, for example, in Example P2.6.

As an alternative it is possible to choose a reaction variant wherein a reducing agent, especially molecular hydrogen, is used, more especially in a mixture of tetrahydrofuran and water as solvent and in the presence of a heavy metal catalyst, especially a Pd catalyst.

Especially preferred conditions for this Process variant are described, for example, in Example P2.5.

Process Variant (E):

Suitable solvents include those mentioned under Variant (B), especially suitable solvents being esters of organic acids, halogenated hydrocarbons and aromatic hydrocarbons; especially two-phase mixtures of an ester with water.

The reactions are advantageously carried out in a temperature range of from 0° C. to the boiling point of the solvent used, preferably from room temperature to 60° C., and in the presence of a base, preferably an inorganic base, for example sodium hydroxide, potassium hydroxide, sodium carbonate or sodium hydrogen carbonate.

Especially preferred conditions for this Process variant are described, for example, in Example P2.3.

In an alternative embodiment, suitable solvents include those mentioned above, preferably ethers, alcohols, water and carboxylic acids, in combination with a hydride, such as a borohydride, especially NaCNBH$_3$.

Especially preferred conditions for this Process variant are described, for example, in Example P2.4.

Process Variant (F):

Examples of solvents and diluents include: aromatic, aliphatic and alicyclic hydrocarbons and halogenated hydrocarbons; ethers, amides and nitriles as listed above under Process variant (A); ketones, such as acetone, methyl ethyl ketone or methyl isobutyl ketone; carboxylic acid esters, such as methyl acetate, ethyl acetate, or esters of benzoic acid; and sulfoxides, such as dimethyl sulfoxide; or mixtures of the mentioned solvents;

especially suitable are esters of organic acids, such as ethyl acetate.

As water-removing agent there are used the customary peptide coupling reagents, especially carbodiimides and hydroxybenzotriazoles.

The reactions are advantageously carried out in a temperature range of from 0° C. to the boiling point of the solvent used, preferably at room temperature.

Especially preferred conditions for the reaction are described, for example, in Example P2.8.

Process Variant (G):

Examples of solvents and diluents include: aromatic, aliphatic and alicyclic hydrocarbons and ethers as listed above under Process variant (A); and sulfoxides, such as dimethyl sulfoxide; or mixtures of the mentioned solvents; ethers, more especially tetrahydrofuran, being especially suitable.

The reactions are advantageously carried out in a temperature range of from 0° C. to the boiling point of the solvent used, preferably from 0° C. to room temperature.

Especially preferred conditions for the reaction are described, for example, in Example P2.10.

Process Variant (H):

Suitable solvents include those mentioned under Variant (B), especially suitable solvents being water, esters of organic acids, halogenated hydrocarbons and aromatic hydrocarbons; especially two-phase mixtures of such an organic solvent with water.

The reactions are advantageously carried out in a temperature range of from 0° C. to the boiling point of the solvent used, preferably from 90° C. to the boiling point of the solvent, and in the presence of a base, preferably an inorganic base, for example sodium hydroxide, potassium hydroxide, sodium carbonate or sodium hydrogen carbonate.

Especially preferred conditions for the reaction are described, for example, in Example P3.2.

Process Variant (I):

Suitable solvents include those mentioned under Variant (B), especially suitable solvents being water, esters of organic acids, halogenated hydrocarbons and aromatic hydrocarbons; especially two-phase mixtures of such an organic solvent with water.

The reactions are advantageously carried out in a temperature range of from 0° C. to the boiling point of the solvent used, preferably from 90° C. to the boiling point, and in the presence of a base, preferably an inorganic base, for example sodium hydroxide, potassium hydroxide, sodium carbonate or sodium hydrogen carbonate.

Especially preferred conditions for the reaction are described, for example, in Example P3.1.

Process Variant (J):

Suitable solvents include those mentioned under Variant (B), especially suitable solvents being water, ethers of organic acids, alcohols and water; especially two-phase mixtures of an ether with water.

The reactions are advantageously carried out in a temperature range of from 0° C. to the boiling point of the solvent used, preferably at room temperature.

Especially preferred conditions for the reaction are described, for example, in Example P3.3.

The compounds of formula (I) may be in the form of one of the possible isomers or in the form of a mixture thereof, in the form of pure isomers or in the form of an isomeric mixture, i.e. in the form of a racemic mixture; the invention relates both to the pure isomers and to the racemic mixtures and is to be interpreted accordingly hereinabove and herein-below, even if stereochemical details are not mentioned specifically in every case.

The racemates can be resolved into the optical antipodes by known methods, for example by recrystallisation from an optically active solvent, by chromatography on chiral adsorbents, for example high pressure liquid chromatography (HPLC) on acetylcellulose, with the aid of suitable microorganisms, by cleavage with specific, immobilised enzymes, or via the formation of inclusion compounds, for example using chiral crown ethers, only one isomer being complexed.

Apart from by separation of corresponding mixtures of isomers, pure optical isomers can be obtained according to the invention also by generally known methods of enantioselective synthesis, for example by carrying out the process according to the invention using starting materials having correspondingly suitable stereochemistry.

In each case it is advantageous to isolate or synthesise the biologically more active isomer, where the individual components have different biological activity.

The compounds of formula (I) may also be obtained in the form of their hydrates and/or may include other solvents, for example solvents which may have been used for the crystallisation of compounds in solid form.

The invention relates to all those embodiments of the process according to which a compound obtainable as starting material or intermediate at any stage of the process is used as starting material and some or all of the remaining steps are carried out or a starting material is used in the form of a derivative or salt and/or its racemates or antipodes or, especially, is formed under the reaction conditions.

In the processes of the present invention it is preferable to use those starting materials and intermediates which result in the compounds of formula (I) that are especially preferred.

The invention relates especially to the preparation processes described in Examples P1.1 to P4.3.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and representatives of the order Acarina, nematodes, cestodes and trematodes, while at the same time protecting useful organisms. The insecticidal or acaricidal activity of the active ingredients according to the invention may manifest itself directly, i.e. in the mortality of the pests, which occurs immediately or only after some time, for example during moulting, or indirectly, for example in reduced ovi-position and/or hatching rate, good activity corresponding to a mortality of at least 50 to 60%.

The said animal pests include, for example, those mentioned in European Patent Application EP-A-736 252, page 5, line 55, to page 6, line 55. The pests mentioned therein are therefore included by reference in the subject matter of the present invention.

It is also possible to control pests of the class Nematoda using the compounds according to the invention. Such pests include, for example, root knot nematodes, cyst-forming nematodes and also stem and leaf nematodes;

especially of *Heterodera* spp., e.g. *Heterodera schachtii*, *Heterodora avenae* and *Heterodora trifolii*; *Globodera* spp., e.g. *Globodera rostochiensis*; *Meloidogyne* spp., e.g. *Meloidogyne incognita* and *Meloidogyne javanica*; *Radopholus* spp., e.g. *Radopholus simiis*; *Pratylenchus*, e.g. *Pratylenchus neglectans* and *Pratylenchus penetrans*; *Tylenchulus*, e.g. *Tylenchulus semipenetrans*; *Longidorus*, *Trichodorus*, *Xiphinema*, *Ditylenchus*, *Apheenchoides* and *Anguina*; insbesondere *Meloidogyne*, e.g. *Meloidogyne incognita*, and *Heterodera*, e.g. *Heterodera glycines*.

An especially important aspect of the present invention is the use of the compounds of formula (I) according to the invention in the protection of plants against parasitic feeding pests.

The compounds according to the invention can be used to control, i.e. to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g. pomes, stone fruit and soft fruit, such as apples, pears, plums, peaches, almonds, cherries and berries, e.g. strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; and tobacco, nuts, coffee, aubergines, sugar cane, tea, pepper, vines, hops, bananas, natural rubber plants and ornamentals.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from attack by fleas, ticks and nematodes.

The invention therefore relates also to pesticidal compositions, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprise at least one of the compounds according to the invention, the choice of formulation being made in accordance with the intended objectives and the prevailing circumstances.

The active ingredient is used in those compositions in pure form, a solid active ingredient, for example, in a specific particle size, or preferably together with at least one of the adjuvants customary in formulation technology, such as extenders, e.g. solvents or solid carriers, or surface-active compounds (surfactants). In the area of parasite control in humans, domestic animals, productive livestock and pets it will be self-evident that only physiologically tolerable additives are used.

As formulation adjuvants there are used, for example, solid carriers, solvents, stabilisers, "slow release" adjuvants, colourings and optionally surface-active substances (surfactants). Suitable carriers and adjuvants include all substances customarily used. As adjuvants, such as solvents, solid carriers, surface-active compounds, non-ionic surfactants, cationic surfactants, anionic surfactants and further adjuvants in the compositions used according to the invention, there come into consideration, for example, those described in EP-A-736 252, page 7, line 51 to page 8, line 39.

The compositions for use in crop protection and in humans, domestic animals and productive livestock generally comprise from 0.1 to 99%, especially from 0.1 to 95%, of active ingredient and from 1 to 99.9%, especially from 5 to 99.9%, of at least one solid or liquid adjuvant, the composition generally including from 0 to 25%, especially from 0.1 to 20%, of surfactants (%= % by weight in each case). Whereas commercial products will preferably be formulated as concentrates, the end user will normally employ dilute formulations having considerably lower concentrations of active ingredient.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons and Bacillus thuringiensis preparations.

Examples of especially suitable mixing partners include: azamethiphos; chlorfenvinphos; bupirimate; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a substance obtainable from the *Bacillus thuringiensis* strain GC91 or from NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; alpha-cypermethrin; zeta-cypermethrin; deltamethrin; diflubenzuron; endosulfan; ethiofencarb; fenitrothion; fenazaquin; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; abamectin; fenobucarb; tebufenozide; fipronil; beta-cyfluthrin; silafluofen; fenpyroximate; pyridaben; primicarb; pyriproxyfen; pyrimidifen; nematorin; nitenpyram; NI-25, acetamiprid; avermectin $B_1$ (abamectin); an insect-active extract from a plant; a preparation comprising insect-active nematodes; a preparation obtainable from Bacillus subtilis; a preparation comprising insect-active fungi; a preparation comprising insect-active viruses; AC 303 630; acephate; acrinathrin; alanycarb; alphamethrin; amitraz; AZ 60541; azinphos A; azinphos M; azocyclotin; bendiocarb; bensultap; betacyfluthrin; BPMC; brofenprox; bromophos A; bufencarb; butocarboxim; butylpyridaben; cadusafos; carbaryl; carbophenothion; chloethocarb; chlorethoxyfos; chlormephos; cis-res-methrin; clocythrin; clofentezine; cyanophos; cyclicprothrin; cyhexatin; demeton M; demeton S; demeton-S-methyl; dichlofenthion; dicliphos; diethion; dimethoate; dimethylvinphos; dioxathion; edifenphos; emamectin; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; lambda-cyhalothrin; malathion; mecarbam; mesulfenphos; metaldehyd; metotcarb; milbemectin; moxidectin; naled; NC 184; omethoate; oxamyl; oxydemethon M; oxydeprofos; permethrin; phenthoate; phorate; phosmet; phoxim; pirimiphos M; pirimiphos A; promecarb; propaphos; prothiofos; prothoate; pyrachlophos; pyrada-phenthion; pyresmethrin; pyrethrum; RH 5992; salithion; sebufos; sulfotep; sulprofos; tebufenpyrad; tebupirimphos; tefluthrin; temephos; terbam; tetrachlorvinphos; thiacloprid; thiamethoxam; thiafenox; thiodicarb; thiofanox; thionazin; thuringiensin; tralomethrin; triarathen; triazophos; triazuron; trichlorfon; triflumuron; trimethacarb; vamidothion; xylylcarb; YI 5301/5302; zetamethrin; DPX-MP062; RH-2485; D 2341 or XMC (3,5-xylyl methylcarbamate).

Preferred crop protection products have especially the following compositions (%= percent by weight):

| Emulsifiable concentrates: | |
| --- | --- |
| active ingredient: | 1 to 90%, preferably 5 to 20% |
| surfactant: | 1 to 30%, preferably 10 to 20% |
| solvent: | 5 to 98%, preferably 70 to 85% |
| Dusts: | |
| active ingredient: | 0.1 to 10%, preferably 0.1 to 1% |
| solid carrier: | 99.9 to 90%, preferably 99.9 to 99% |
| Suspension concentrates: | |
| active ingredient: | 5 to 75%, preferably 10 to 50% |
| water: | 94 to 24%, preferably 88 to 30% |
| surfactant: | 1 to 40%, preferably 2 to 30% |
| Wettable powders: | |
| active ingredient: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| active ingredient: | 0.5 to 30%, preferably 3 to 15% |
| solid carrier: | 99.5 to 70%, preferably 97 to 85% |

The compositions according to the invention may also comprise further solid or liquid adjuvants, such as stabilisers, e.g. vegetable oils or epoxidised vegetable oils (e.g. epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g. acaricides, bactericides, fungicides, nematicides, molluscicides or selective herbicides.

The crop protection products according to the invention are prepared in known manner, in the absence of adjuvants, e.g. by grinding, sieving and/or compressing a solid active ingredient or mixture of active ingredients, for example to a certain particle size, and in the presence of at least one adjuvant, for example by intimately mixing and/or grinding the active ingredient or mixture of active ingredients with the adjuvant (s). The invention relates likewise to those processes for the preparation of the compositions according to the invention and to the use of the compounds of formula (I) in the preparation of those compositions.

The invention relates also to the methods of application of the crop protection products, i.e. the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example into the soil, e.g. in granular form (soil application). In the case of paddy rice crops, such granules may be applied in metered amounts to the flooded rice field.

The crop protection products according to the invention are also suitable for protecting plant propagation material, e.g. seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example to the seed furrow during sowing. The invention relates also to such methods of treating plant propagation material and to the plant propagation material so treated.

PREPARATION EXAMPLES

Example P1.1 4"-Desoxy-4"-epi-(N-3-fluorophenyl-methyl-amino)-avermectin B1

1.0 g of 4"-desoxy-4"-epi-amino-avermectin B1 is dissolved in 12 ml of tetrahydrofuran. 1.8 ml of acetic acid, 0.2 ml of water and 0.18 ml of 3-fluorobenzaldehyde are added. 90 mg of sodium cyanoborohydride are then added. The mixture is stirred at room temperature for 12 hours. Extraction is then carried out with ethyl acetate and saturated sodium chloride solution; the organic phase is dried over sodium sulfate and the solvents are distilled off. The residue is purified by chromatography on silica gel (hexane/ethyl acetate), yielding 4"-desoxy-4"-epi-(N-3-fluorophenylmethyl-amino)-avermectin B1.

Example P1.2 4"-Desoxy-4"-epi-N-ethylamino-avermectin B1

4.0 g of 4"-desoxy-4"-epi-amino-avermectin B1 are dissolved in 24 ml of ethyl acetate. 7.4 ml of ethyl iodide and 24 ml of sodium bicarbonate (1N in water) are added. The mixture is stirred vigorously at room temperature for 14 hours. The phases are then separated; the organic phase is dried over sodium sulfate and the solvents are distilled off. The residue is purified by chromatography on silica gel (hexane/ethyl acetate), yielding 4"-desoxy-4"-epi-N-ethylamino-avermectin B1.

Example P1.3 4"-Desoxy-4"-epi-N-(isopropoxycarbonyl-methyl)-amino-avermectin B1

300 mg of 4"-desoxy-4"-epi-amino-avermectin B1 are dissolved in 3 ml of ethyl acetate. 620 mg of isopropyl bromoacetate and 3 ml of sodium bicarbonate (1N in water) are added. The mixture is stirred vigorously at room temperature for 18 hours. The phases are then separated; the organic phase is dried over sodium sulfate and the solvent is distilled off. The residue is purified by chromatography on silica gel (hexane/ethyl acetate), yielding 4"-desoxy-4"-epi-N-(isopropoxycarbonyl-methyl)-amino-avermectin B1.

Example P2.1 4"-Desoxy-4"-epi-(N-methyl-N-1-propen-3-yl-amino)-avermectin B1

600 mg of 4"-desoxy-4"-epi-methylamino-avermectin B1 are dissolved in 6 ml of ethyl acetate. 0.56 ml of allyl bromide and 6 ml of sodium bicarbonate (1N in water) are added. The mixture is stirred vigorously at 60° C. for 18 hours, then cooled. The phases are then separated; the organic phase is dried over sodium sulfate and the solvent is distilled off. The residue is purified by chromatography on silica gel (hexane/ethyl acetate), yielding 4"-desoxy-4"-epi-(N-methyl-N-1-propen-3-yl-amino)-avermectin B1.

Example P2.2 4"-Desoxy-4"-epi-(N-2-hydroxyethyl-N-methylamino)-avermectin B1

Step 1: 4.55 g of 4"-desoxy-4"-epi-methylamino-avermectin B1 are dissolved in 45 ml of ethyl acetate. 8.6 g of ethyl bromoacetate and 45 ml of sodium bicarbonate (1N in water) are added. The mixture is stirred vigorously at 60° C. for 18 hours, then cooled. The phases are then separated; the organic phase is dried over sodium sulfate and the solvent is distilled off. The residue is purified by chromatography on silica gel (hexane/ethyl acetate), yielding 4"-desoxy-4"-epi-(N-methyl-N-ethoxycarbonylmethyl-amino)-avermectin B1.

Step 2: 300 mg of 4"-desoxy-4"-epi-(N-methyl-N-ethoxycarbonylmethyl-amino)-avermectin B1 are dissolved in 6 ml of toluene. With stirring at room temperature, 1.3 ml of diisobutylaluminium hydride (1.2 mol/l in toluene) are added. After 15 minutes, extraction is carried out with ethyl acetate and saturated ammonium chloride solution. The phases are then separated; the organic phase is dried over sodium sulfate and the solvent is distilled off. The residue is purified by chromatography on silica gel (ethyl acetate/methanol), yielding 4"-desoxy-4"-epi-(N-2-hydroxyethyl-N-methylamino)-avermectin B1.

Example P2.3 4"-Desoxy-4"-epi-(N-isopropyl-N-methylamino)-avermectin B1

2.0 g of 4"-desoxy-4"-epi-isopropylamino-avermectin B1 are dissolved in 20 ml of ethyl acetate. 4 ml of methyl iodide and 20 ml of sodium bicarbonate (1N in water) are added and the mixture is stirred vigorously at 60° C. for 14 hours, then cooled. The phases are then separated; the organic phase is dried over sodium sulfate and the solvent is distilled off. The residue is purified by chromatography on silica gel (ethyl acetate), yielding 4"-desoxy-4"-epi-(N-isopropyl-N-methylamino)-avermectin B1.

Example P2.4 4"-Desoxy-4"-epi-(N-isopropyl-N-methylamino)-avermectin B1

9.14 g of 4"-desoxy-4"-epi-isopropylamino-avermectin B1 are dissolved in 100 ml of methanol. 15 ml of pivalic acid and 25 ml of formaldehyde solution (37% in water) are added. 0.7 g of sodium cyanoborohydride is then added. The mixture is stirred at room temperature for 1 hour, then the methanol is evaporated off in vacuo and the residue is extracted with ethyl acetate and saturated sodium bicarbonate solution. The phases are then separated; the organic phase is dried over sodium sulfate and the solvent is distilled off. The residue is purified by chromatography on silica gel (ethyl acetate/methanol), yielding 4"-desoxy-4"-epi-(N-isopropyl-N-methylamino)-avermectin B1.

Example P2.5 4"-Desoxy-4"-epi-(N-carboxymethyl-N-methylamino)-avermectin B1

Step 1: 10 g of 4"-desoxy-4"-epi-methylamino-avermectin B1 are dissolved in 100 ml of ethyl acetate. 15.6 g of benzyl bromoacetate and 100 ml of sodium bicarbonate (1N in water) are added. The mixture is stirred vigorously at 60° C. for 5 days, then cooled. The phases are then separated; the organic phase is dried over sodium sulfate and the solvent is distilled off. The residue is purified by chromatography on silica gel (hexane/ethyl acetate), yielding 4"-desoxy-4"-epi-(N-benzyloxycarbonyl-methyl-N-methylamino)-avermectin B1.

Step 2: 7.8 g of 4"-desoxy-4"-epi-(N-benzyloxycarbonyl-methyl-N-methylamino)-avermectin B1 are dissolved in 100 ml of tetrahydrofuran. 780 mg of palladium (5% on carbon) are added and hydrogenation is carried out at normal pressure and room temperature. After one hour the absorption of hydrogen has ceased. The mixture is filtered over Celite and the solvent is evaporated off, yielding 4"-desoxy-4"-epi-(N-carboxymethyl-N-methylamino)-avermectin B1.

Example P2.6 4"-Desoxy-4"-epi-(N-carboxymethyl-N-methylamino)-avermectin B1

Step 1: 15 g of 4"-desoxy-4"-epi-methylamino-avermectin B1 are dissolved in 120 ml of ethyl acetate. 26 g of methyl bromoacetate and 120 ml of sodium bicarbonate (1N in water) are added. The mixture is stirred vigorously at 60° C. for 5 days, then cooled. The phases are then separated; the organic phase is dried over sodium sulfate and the solvent is distilled off. The residue is purified by chromatography on silica gel (hexane/ethyl acetate), yielding 4"-desoxy-4"-epi-(N-methoxycarbonyl-methyl-amino-N-methyl)-avermectin B1.

Step 2: 10 g of 4"-desoxy4"-epi-(N-methoxycarbonylmethyl-amino-N-methyl)-avermectin B1 are dissolved in 90 ml of tetrahydrofuran. 10 ml of water and 440 mg of lithium hydroxide monohydrate are added and stirring is carried out at room temperature for 14 hours. Extraction is then carried out with water and diethyl ether, and the aqueous phase is separated off and lyophilised. The residue is extracted with ethyl acetate and citric acid (10% in water); the organic phase is dried over sodium sulfate and the solvent is distilled off, yielding 4"-desoxy-4"-epi-(N-carboxymethyl-N-methylamino)-avermectin B1.

Example P2.7 4"-Desoxy-4"-epi-(N-ethyl-N-methylamino)-avermectin B1

8.0 g of 4"-desoxy-4"-epi-N-methylamino-avermectin B1 are dissolved in 50 ml of ethyl acetate. 15 ml of ethyl iodide and 50 ml of sodium bicarbonate (1N in water) are added. The mixture is stirred vigorously at 60° C. for 2 days. The phases are then separated; the organic phase is dried over sodium sulfate and the solvents are distilled off. The residue is purified by chromatography on silica gel (ethyl acetate/methanol), yielding 4"-desoxy-4"-epi-(N-ethyl-N-methylamino)-avermectin B1.

Example P2.8 4"-Desoxy-4"-epi-{N-[(1-benzyloxycarbonyl-ethylcarbamoyl)-methyl]-N-methylamino}-avermectin B1

500 mg of 4"-desoxy-4"-epi-(N-carboxymethyl-N-methylamino)-avermectin B are dissolved in 5 ml of ethyl acetate, then 170 mg of L-alanine benzyl ester, 72 mg of 1-hydroxy-7-aza-benzotriazole and 110 mg of N,N-dicyclohexylcarbodiimide are added. Stirring is carried out at room temperature for 7 days. The mixture is then extracted with ethyl acetate and sodium bicarbonate (1N in water); the organic phase is dried over sodium sulfate and the solvent is distilled off. The residue is purified by chromatography on silica gel (hexane/ethyl acetate), yielding 4"-desoxy-4"-epi-{N-[(1-benzyloxycarbonyl-ethylcarbamoyl)-methyl]-N-methylamino}-avermectin B1.

Example P2.9 4"-Desoxy-4"-epi-{N-[(1-carboxyethylcarbamoyl)-methyl]-N-methyl-amino}-avermectin B1

160 mg of 4"-desoxy-4"-epi-{N-[(1-benzyloxycarbonyl-ethylcarbamoyl)-methyl]-N-methylamino}-avermectin B1 are dissolved in 10 ml of tetrahydrofuran. 50 mg of palladium (5% on carbon) are added and hydrogenation is carried out at normal pressure and room temperature. After 3 hours the absorption of hydrogen has ceased. The mixture is filtered over Celite and the solvent is evaporated off, yielding 4"-desoxy-"-epi-{N-[(1-carboxy-ethyl-carbamoyl)-methyl]-N-methylamino}-avermectin B1.

Example P2.10 4"-Desoxy-4"-epi-[N-(2-hydroxy-2-methyl-propyl)-N-methylamino]-avermectin B1

300 mg of 4"-desoxy-4"-epi-(N-methyl-N-ethoxycarbonylmethyl-amino)-avermectin B1 (Step 1 from P2.2) are dissolved in 6 ml of tetrahydrofuran. With stirring at room temperature, 0.64 ml of methylmagnesium bromide (3 mol/l in diethyl ether) is added. After one hour, extraction is carried out with ethyl acetate and saturated ammonium chloride solution. The phases are then separated; the organic phase is dried over sodium sulfate and the solvents are distilled off. The residue is purified by chromatography on silica gel (ethyl acetate/methanol), yielding 4"-desoxy-4"-epi-[N-(2-hydroxy-2-methyl-propyl)-N-methyl-amino]-avermectin B1.

Example P3.1 4"-Desoxy-4"-epi-[N,N-bis(1-phenyl-1-propen-3-yl)amino]-avermectin B1

3.48 g of 4"-desoxy-4"-epi-amino-avermectin B1 are dissolved in 40 ml of ethyl acetate. 4.62 g of 3-bromo-1-phenyl-1-propene and 40 ml of sodium bicarbonate (1N in water) are added. The mixture is stirred vigorously at 60° C. for 3 days and then cooled. The phases are then separated; the organic phase is dried over sodium sulfate and the solvent is distilled off. The residue is purified by chromatography on silica gel (hexane/ethyl acetate) yielding 4"-desoxy-4"-epi-[N,N-bis(1-phenyl-1-propen-3-yl)amino]-avermectin B1.

Example P3.2 4"-Desoxy-4"-epi-(azetidin-1-yl)-avermectin B1

300 mg of 4"-desoxy-4"-epi-amino-avermectin B1 are dissolved in 1 ml of toluene. 0.106 ml of 1,3-dibromopropane and 1 ml of sodium bicarbonate (1N in water) are added. The mixture is stirred vigorously at 90° C. for 24 hours, then cooled. The phases are then separated; the organic phase is dried over sodium sulfate and the solvent is distilled off. The residue is purified by chromatography on silica gel (ethyl acetate/methanol), yielding 4"-desoxy-4"-epi-(azetidin-1-yl)-avermectin B1.

Example P3.3: 4"-Desoxy-4"-epi-[N,N-bis(3,3-dimethyl-butyl)amino]-avermectin B1

0.87 g of 4"-desoxy-4"-epi-amino-avermectin B1 is dissolved in 10 ml of tetrahydrofuran. 1 ml of pivalic acid, 0.1 ml of water and 0.60 9 of 3,3-dimethylbutyraldehyde are added. 0.38 g of sodium cyanoborohydride is then added. The mixture is stirred at room temperature for 14 hours. Extraction is then carried out with ethyl acetate and sodium bicarbonate (1N in water); the organic phase is dried over sodium sulfate and the solvents are distilled off. The residue is purified by chromatography on silica gel (hexane/ethyl acetate), yielding 4"-desoxy-4"-epi-[N,N-bis(3,3-dimethyl-butyl)amino]-avermectin B1.

P4.1 4"-Desoxy-4"-epi-[N-(3-acetoxy-propyl)-N-methylamino]-avermectin B1

100 mg 4"-desoxy-4"-epi-[N-(3-iodo-propyl)-N-methylamino]-avermectin B1 and 100 mg sodiumacetate are dissolved in 2 ml N,N-dimethylformamide. The mixture is heated to 60° C. and stirred at this temperature for 90 minutes. The mixture is then cooled to room temperature and extracted with diethylether. The organic layer is separated, washed with sodium bicarbonate (1N in water) and dried over sodiumsulfate. The solvent is distilled off and the residue purified over silica gel using hexane/ethylacetate as en eluent, yielding 4"-desoxy4"-epi-[N-(3-acetoxy-propyl)-N-methylamino]-avermectin B1.

P4.2 4"-Desoxy-4"-epi-[N-(3-iodo-propyl)-N-methylamino]-avermectin B1

3 g 4"-Desoxy-4"-epi-N-methylamino-avermectin B1 and 9 ml 1,3-diiodopropane are dissolved in 9 ml ethylacetate. 18 ml of sodium bicarbonate solution (1N in water) are added and the mixture stirred for three days at 60 ° C. The mixture is then cooled to room temperature, the organic layer separated and dried over sodiumsulfate. The solvent is distilled off and the residue purified over silica gel using hexane/ethylacetate as en eluent, yielding 4"-Desoxy-4"-epi-[N-(3-iodo-propyl)-N-methylamino]-avermectin B1.

P4.3 4"-Desoxy-4"-epi-N-(2-cyano-ethylamino)-avermectin B1

872 mg 4"-desoxy-4"-epi-N-amino-avermectin B1 are dissolved in 5 ml methanol. 212 mg acrylonitrile are added and the mixture stirred for three days at room temperature. The solvent is then distilled off and the residue purified over silica gel using hexane/ethylacetate as en eluent, yielding 4"-Desoxy-4"-epi-N-(2-cyano-ethylamino)-avermectin B1.

Similarly to the preparation examples above it is also possible to prepare the compounds listed in Tables 1 to 3. In the tables, the ⁓ symbol denotes the bond through which the radical in question is attached to the nitrogen atom of the skeleton.

Since in most cases the compounds are present as mixtures of the avermectin derivatives B1a and B1b, characterization by customary physical data such as melting point or refractive index makes little sense. For this reason, the compounds are characterized by the retention times which are determined in an analysis by HPLC (high performance liquid chromatography). Here, the term B1a refers to the main component in which $R_1$ is sec-butyl, with a content of usually more than 80%. B1b denotes the minor component in which $R_1$ is isopropyl. The compounds where two retention times are given both for the B1a and for the B1b derivative are mixtures of diastereomers which can be separated chromatographically. In the case of compounds where a retention time is given only in column B1a or only in column B1a or B1b component, respectively, can be obtained during work-up. The correct structures of the B1a and B1b components are assigned by mass spectrometry.

The following method is used for HPLC analysis:

| HPLC gradient conditions | | | |
|---|---|---|---|
| Solvent A: | 0.01% of trifluoroacetic acid in $H_2O$ | | |
| Solvent B: | 0.01% of trifluoroacetic acid in $CH_3CN$ | | |
| Time [min] | A [%] | B [%] | Flow rate [µl/min] |
| 0 | 80 | 20 | 500 |
| 0.1 | 50 | 50 | 500 |
| 10 | 5 | 95 | 500 |
| 15 | 0 | 100 | 500 |
| 17 | 0 | 100 | 500 |
| 17.1 | 80 | 20 | 500 |
| 22 | 80 | 20 | 500 |
| Type of column | YMC-Pack ODS-AQ | | |
| Column length | 125 mm | | |
| Internal diameter of column: | 2 mm | | |
| Temperature | 40° C. | | |

The YMC-Pack ODS-AQ column used for the chromatography of the compounds is manufactured by YMC, Alte Raesfelderstrasse 6, 46514 Schermbeck, Germany.

TABLE 1

Compounds of the formula (I) in which $R_1$ is sec-butyl (B1a) or isopropyl (B1b) and $R_2$ is hydrogen.

| No. | $R_3$ | Retention time (min) B1a | B1b |
|---|---|---|---|
| 1.1 | 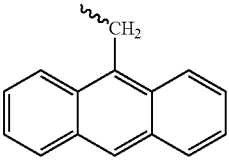 | 7.64 | 7.06 |
| 1.2 | 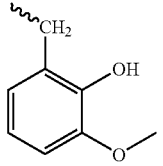 | 5.92 | 5.62 |
| 1.3 | (3-nitrophenyl)methyl | 5.80 | 5.59 |
| 1.4 | (4-dimethylaminophenyl)methyl | 6.12 | 5.87 |
| 1.5 | (3-bromophenyl)methyl | 6.32 | 6.00 |
| 1.6 | | 5.84 | 5.48 |
| 1.7 | 2-phenyl-n-propyl | 6.62/ | 6.20/ |

TABLE 1-continued

Compounds of the formula (I) in which $R_1$ is sec-butyl (B1a) or isopropyl (B1b) and $R_2$ is hydrogen.

| No. | $R_3$ | Retention time (min) B1a | B1b |
|---|---|---|---|
| 1.8 | 3-pyridylmethyl | 6.41 | 6.00 |
| 1.9 | (2,4-dimethylphenyl)methyl | 5.96 | 5.61 |
| 1.10 | (3-fluorophenyl)methyl | 6.59 | 6.22 |
|  |  | 5.80 | 5.46 |
| 1.11 | (neopentyl –CH₂–C(CH₃)₃) | 6.18 | 5.87 |
| 1.12 | (3-carboxyphenyl)methyl | 5.39 | 5.14 |
| 1.13 | (phenanthren-9-yl)methyl | 7.11 | 6.72 |
| 1.14 | (3,4-methylenedioxy-6-nitrophenyl)methyl | 6.01 | 5.66 |
| 1.15 | (4-methoxynaphth-1-yl)methyl | 8.37 | 7.75 |
| 1.16 | (2-hydroxy-5-methoxyphenyl)methyl | 5.64 | 5.26 |
| 1.17 | (2-hydroxy-4-methoxyphenyl)methyl | 5.81 | 5.55 |
| 1.18 | (2,3-dihydroxyphenyl)methyl | 5.45 | 5.10 |
| 1.19 | (2-hydroxy-5-nitrophenyl)methyl | 6.28 | 5.92 |
| 1.20 | (2-methoxynaphth-1-yl)methyl | 6.73 | 6.34 |
| 1.21 | dec-4-en-1-yl | 7.96 | 7.54 |
| 1.22 | (3-[4-methoxyphenoxy]phenyl)methyl | 7.00 | 6.62 |
| 1.23 | isobutyl (–CH₂–CH(CH₃)₂) | 6.63 | 6.25 |
| 1.24 | 3-phenyl-n-propyl | 7.03 | 6.65 |
| 1.25 | 4-pyridylmethyl | 5.40 | 5.07 |
| 1.26 | (4-methyl-1H-imidazol-5-yl)methyl | 4.57 | 4.32 |
| 1.27 | ethyl | 5.30 | 4.96 |
| 1.28 | n-butyl | 5.56 | 5.10 |
| 1.29 | (E)-cinnamyl (–CH₂–CH=CH–phenyl) | 5.95 | 5.60 |
| 1.30 | (2-bromophenyl)methyl | 6.85 | 6.47 |
| 1.31 | (1H-imidazol-2-yl)methyl | 5.24 | 4.86 |
| 1.32 | (5-methylfuran-2-yl)methyl | 5.74 | 5.36 |
| 1.33 | (4-n-propoxyphenyl)methyl | 6.49 | 6.10 |
| 1.34 | (4-styrylphenyl)methyl | 7.18 | — |
| 1.35 | (2-chloro-4-hydroxyphenyl)methyl | 6.30 | 5.87 |
| 1.36 | cyclododecyl | 9.2 | 8.80 |
| 1.37 | 1-methyl-n-butyl | 6.76/6.98 | 6.33/6.50 |
| 1.38 | 4-hydroxy-1-methyl-n-butyl | 6.25 | 5.70 |
| 1.39 | 1-methyl-n-propyl | 7.50 | 6.81 |
| 1.40 | (3,7-dimethyl-7-hydroxyoctyl –CH₂–CH(CH₃)–CH₂CH₂CH₂–C(CH₃)₂OH) | 6.50 | 6.10 |
| 1.41 | (4-tert-butylphenyl)methyl | 7.31 | 6.98 |
| 1.42 | 3-phenyl-n-butyl | 7.22 | 6.90 |
| 1.43 | (4-benzyloxyphenyl)methyl | 6.84 | 6.56 |
| 1.44 | —CH₂—C(═O)—O—CH₂-phenyl | 7.15 | 6.76 |
| 1.45 | —CH₂—C(═O)—O-methyl | 5.75 | 5.39 |
| 1.46 | —CH₂—C(═O)—O-ethyl | 6.12 | 5.72 |
| 1.47 | 1-methyl-3-oxo-n-butyl | 6.95 | 6.41 |
| 1.48 | 1-(1-methylcyclopropyl)ethyl | 6.40 | 5.96 |

TABLE 1-continued

Compounds of the formula (I) in which $R_1$ is sec-butyl (B1a) or isopropyl (B1b) and $R_2$ is hydrogen.

| No. | $R_3$ | Retention time (min) B1a | B1b |
|---|---|---|---|
| 1.49 | (dimethyl succinate-like group) | 6.27 | 5.81 |
| 1.50 | CH₂—CH=CH—C≡C—C(CH₃)₃ (E) | 5.86 | 5.50 |
| 1.51 | CH₂—CH=CH—C≡C—C(CH₃)₃ (Z) | 5.24 | 5.86 |
| 1.52 | CH(CH₃)CH₂—P(=O)(OCH₃)₂ | 5.35 | 5.00 |
| 1.53 | tetrahydropyran-4-yl | 5.20 | 4.86 |
| 1.54 | 1,2-dimethyl-3-hydroxy-n-propyl | 5.71 | 5.30 |
| 1.55 | cyclobutyl | 5.61 | 5.24 |
| 1.56 | CH(CH₃)—C(=O)—NH—t-Bu | 7.42 | 6.90 |
| 1.57 | CH(CH₃)—CH(OCH₃)₂ | 6.47 | 6.02 |
| 1.58 | —CH₂C(=O)—O-i-propyl | 5.93 | 5.72 |
| 1.59 | —CH₂—C(=O)—O—CH₂—CH₂—O—CH₃ | 5.44 | 5.21 |
| 1.60 | —CH₂C(=O)—O-tert-butyl | 6.15 | 5.97 |
| 1.61 | —CH₂C(=O)NH₂ | 4.83 | 4.58 |
| 1.62 | CH(CH₃)—C(=O)—OCH₃ | 6.13 | 5.67 |
| 1.63 | CH₂—(CHOH)₄—CH₂OH | 3.46 | 3.26 |
| 1.64 | propargyl | 5.36 | 4.97 |
| 1.65 | 2-chloroallyl | 5.93 | 5.51 |
| 1.66 | 3,3-dichloroallyl | 6.12 | 5.72 |
| 1.67 | CH₂—(2-chlorothiazol-5-yl) | 5.97 | 5.59 |
| 1.68 | CH₂—(6-chloropyridin-3-yl) | 5.57 | 5.24 |
| 1.69 | CH(CH₃)—CH₂—OCH₃ | | |
| 1.70 | CH₂—(furan-2-yl) | | |
| 1.71 | 1-cyclopropylethyl | | |
| 1.72 | tetrahydrothiopyran-4-yl | | |
| 1.73 | CH(CH₃)—C(=O)—O—ethyl | | |
| 1.74 | CH(CH₃)—CH₂—C(=O)OH | | |
| 1.75 | 2,2-dimethyl-n-propyl | | |
| 1.76 | CH(C₂H₅)₂ | | |
| 1.77 | CH(CH₃)—CH(CH₃)₂ | | |
| 1.78 | CH(CF₃)—CH₂—C(=O)—O-ethyl | | |
| 1.79 | 3-methylcyclopentyl | | |

TABLE 1-continued

Compounds of the formula (I) in which $R_1$ is sec-butyl (B1a) or isopropyl (B1b) and $R_2$ is hydrogen.

| No. | $R_3$ | Retention time (min) B1a | B1b |
|---|---|---|---|
| 1.80 | 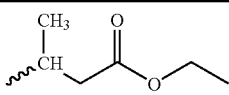 | | |
| 1.81 | 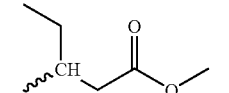 | | |
| 1.82 | 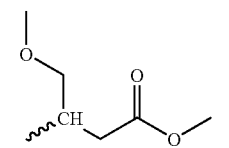 | | |
| 1.83 | (pentafluorophenyl)methyl | | |
| 1.84 | (2,3,5-trichlorophenyl)methyl | | |
| 1.85 | (2,3,6-trichlorophenyl)methyl | | |
| 1.86 | (2,3,4-trifluorophenyl)methyl | | |
| 1.87 | (2,6-dichlorophenyl)methyl | | |
| 1.88 | (2,3-dichlorophenyl)methyl | | |
| 1.89 | (2-hydroxy-3,5-dichlorophenyl)methyl | | |
| 1.90 | (2-chloro-6-fluorophenyl)methyl | | |
| 1.91 | (2-chloro-6-nitrophenyl)methyl | | |
| 1.92 | (3-chloro-4-nitrophenyl)methyl | | |
| 1.93 | (2-chloro-5-nitrophenyl)methyl | | |
| 1.94 | (2,6-difluorophenyl)methyl | | |
| 1.95 | (2,3-difluorophenyl)methyl | | |
| 1.96 | (2-hydroxy-5-bromophenyl)methyl | | |
| 1.97 | (2-hydroxy-5-chlorophenyl)methyl | | |
| 1.98 | (3-nitro-4-hydroxyphenyl)methyl | | |
| 1.99 | (3-hydroxy-4-nitrophenyl)methyl | | |
| 1.100 | (3-hydroxyphenyl)methyl | | |
| 1.101 | (2-hydroxyphenyl)methyl | | |
| 1.102 | (2,5-dihydroxyphenyl)methyl | | |
| 1.103 | 3-trifluoromethylcyclohexyl | | |
| 1.104 | 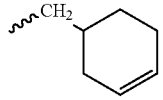 | | |
| 1.105 | 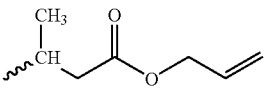 | | |
| 1.106 | 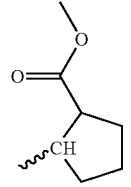 | | |
| 1.107 | 2-methoxycyclohexyl | | |
| 1.108 | 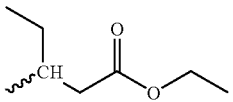 | | |
| 1.109 | 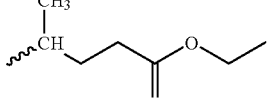 | | |
| 1.110 | 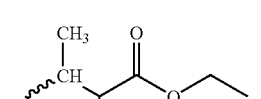 | | |
| 1.111 |  | | |
| 1.112 | 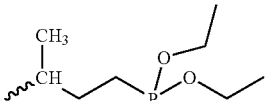 | | |
| 1.113 | (2-trifluoromethylphenyl)methyl | | |
| 1.114 | (3-trifluoromethoxyphenyl)methyl | | |
| 1.115 | (3-cyanophenyl)methyl | | |
| 1.116 | (2,3-methylenedioxyphenyl)methyl | | |
| 1.117 | (2-methoxy-5-bromophenyl)methyl | | |
| 1.118 | (3-bromo-4-hydroxy-5-methoxyphenyl)methyl | | |
| 1.119 | (2-nitro-3-methoxyphenyl)methyl | | |
| 1.120 | (4-methoxyphenyl)methyl | | |
| 1.121 | (3-hydroxy-4-methoxyphenyl)methyl | | |
| 1.122 |  | | |
| 1.123 | 2-ethylhexyl | | |
| 1.124 |  | | |
| 1.125 |  | | |
| 1.126 | [4-(1,1,2,2-Tetrafluoro-ethoxy)-phenyl]-methyl | | |
| 1.127 |  | | |

TABLE 1-continued

Compounds of the formula (I) in which $R_1$ is sec-butyl (B1a) or isopropyl (B1b) and $R_2$ is hydrogen.

| No. | $R_3$ | Retention time (min) B1a | B1b |
|---|---|---|---|
| 1.128 | (structure: 4-acetoxybenzyl) | | |
| 1.129 | (3-bromo-4,6-dimethoxyphenyl)methyl | | |
| 1.130 | (2-bromo-4,5-dimethoxyphenyl)methyl | | |
| 1.131 | (structure: 4-acetamidobenzyl) | | |
| 1.132 | (2-nitro-4,5-dimethoxyphenyl)methyl | | |
| 1.133 | 2-benzyloxyethyl | | |
| 1.134 | (3,5-dimethyl-4-hydroxyphenyl)methyl | | |
| 1.135 | (2-hydroxy-4,6-dimethoxyphenyl)methyl | | |
| 1.136 | (structure: ethyl cyclohexanecarboxylate) | | |
| 1.137 | (structure: N-acryloyl aminoalkyl) | | |
| 1.138 | (structure: quinolin-2-ylmethyl) | | |
| 1.139 | (structure: N-phenyl propanamide) | | |
| 1.140 | (2,4,6-trimethylphenyl)methyl | | |
| 1.141 | 3,7-dimethyloct-6-en-1-yl | | |
| 1.142 | naphth-1-yl | | |
| 1.143 | naphth-2-yl | | |
| 1.144 | (structure: 6-methylchromon-3-ylmethyl) | | |
| 1.145 | (structure: 2,6,6-trimethylcyclohex-1-enylmethyl) | | |
| 1.146 | (structure: diethyl 2-methylpentanedioate derivative) | | |
| 1.147 | (structure: antipyrinyl methyl) | | |
| 1.148 | (structure: 4-benzoylpiperidinyl) | | |
| 1.149 | (structure: 4-(3-dimethylaminopropoxy)benzyl) | | |
| 1.150 | (structure: diethyl formamido malonate derivative) | | |
| 1.151 | n-dodecyl | | |
| 1.152 | (3-[3,4-dichlorophenoxy]phenyl)methyl | | |
| 1.153 | (3-[4-chlorophenoxy]phenyl)methyl | | |
| 1.154 | (structure: 4-dimethylaminonaphth-1-ylmethyl) | | |
| 1.155 | (structure: 3-(3-trifluoromethylphenoxy)benzyl) | | |
| 1.156 | (structure: fluoren-2-ylmethyl) | | |

TABLE 1-continued

Compounds of the formula (I) in which $R_1$ is sec-butyl (B1a) or isopropyl (B1b) and $R_2$ is hydrogen.

| No. | $R_3$ | Retention time (min) B1a | B1b |
|---|---|---|---|
| 1.157 | *(4-benzyloxy-3-methoxybenzyl)* | | |
| 1.158 | *(pyren-1-ylmethyl)* | | |
| 1.159 | *(6,6-dimethyl-5,6-dihydro-2H-pyran-2-on-4-yl)* | | |
| 1.160 | *(dimethyl 2-methylenesuccinate-derived)* | 11.03 | 10.39 |
| 1.161 | *(2-cyano-2-phenyl-1-methylvinyl)* | 12.27 | 11.70 |
| 1.162 | *(methyl 4-methyl-2-pentenoate-derived)* | 12.28 | |
| 1.163 | n-propyl | 5.42 | 5.08 |
| 1.164 | Iso-butyl | 5.49 | 5.26 |
| 1.165 | 3,3,3-trifluoromethyl | 5.55 | 5.23 |
| 1.166 | 3-hydroxypropyl | 4.83 | 4.54 |
| 1.167 | *(diethyl malonate-derived)* | 10.79 | 10.24 |
| 1.168 | *(oxiranylmethyl)* | 4.91 | 4.54 |
| 1.169 | n-pentyl | 5.42 | 5.17 |
| 1.170 | n-hexyl | 5.82 | 5.55 |
| 1.171 | n-heptyl | 6.18 | 5.87 |
| 1.172 | n-nonyl | 7.10 | 6.83 |
| 1.173 | n-decyl | 7.53 | 7.21 |
| 1.174 | *(ethyl propanoate-derived)* | 5.12 | 4.79 |
| 1.175 | *(tert-butyl propanoate-derived)* | 5.72 | 5.45 |
| 1.176 | *(2-cyanoethyl)* | 4.57 | 4.18 |
| 1.177 | *(cyanomethyl)* | 9.01 | 8.37 |
| 1.178 | *(2,3-dihydroxypropyl)* | 4.64 | 4.43 |
| 1.179 | *(2,3,4-trihydroxy-5-hydroxymethyl)* | 4.12 | |
| 1.180 | allyl | 4.91 | 4.59 |
| 1.181 | *(3,4,5-trihydroxyhexyl)* | 3.99 | 3.75 |
| 1.182 | *(ethyl 3-methyl-2-butenoate-derived)* | 5.49 | 5.12 |
| 1.183 | *(3-(methylthio)propyl)* | 5.28 | 4.91 |
| 1.184 | *(2,3,4-trihydroxypentyl)* | 4.27 | 4.00 |
| 1.185 | *(carboxymethyl)* | 5.43 | |

TABLE 1-continued

Compounds of the formula (I) in which $R_1$ is sec-butyl (B1a) or isopropyl (B1b) and $R_2$ is hydrogen.

| No. | $R_3$ | Retention time (min) B1a | B1b |
|---|---|---|---|
| 1.186 | (acetamido-trihydroxy-pentyl group) | 4.09 | |
| 1.187 | (2-hydroxy-2-methylpropyl) | 4.98 | 4.67 |
| 1.188 | (3,4-dihydroxypentyl) | 4.16 | 3.89 |
| 1.189 | 2-phenylethyl | 5.49 | 5.12 |
| 1.190 | (2-phthalimidoethyl) | 5.23 | 4.96 |
| 1.191 | —(CH$_2$)$_2$NH$_2$ | | |
| 1.192 | —(CH$_2$)$_2$N(CH$_3$)$_2$ | | |
| 1.193 | (2-(pyrrolidin-1-yl)ethyl) | | |
| 1.194 | (2-(piperidin-1-yl)ethyl) | | |
| 1.195 | (2-(morpholin-4-yl)ethyl) | | |
| 1.196 | (2-(thiomorpholin-4-yl)ethyl) | | |
| 1.197 | (2-(4-methylpiperazin-1-yl)ethyl) | | |
| 1.198 | (2-(4-phenylpiperazin-1-yl)ethyl) | | |
| 1.199 | (2-(4-(ethoxycarbonylmethyl)piperazin-1-yl)ethyl) | | |
| 1.200 | (2-(4-(2-hydroxyethyl)piperazin-1-yl)ethyl) | | |
| 1.201 | (2-(4-(2-hydroxy-2-methylpropyl)piperazin-1-yl)ethyl) | | |
| 1.202 | (4-phthalimidobutyl) | | |
| 1.203 | (2-(2-phthalimidoethoxy)ethyl) | | |

TABLE 2

Compounds of the formula (I) in which $R_1$ is sec-butyl (B1a) or isopropyl (B1b) and $R_2$ is methyl:

| No. | $R_3$ | Retention time (min) B1a | B1b |
|---|---|---|---|
| 2.1 | Benzyl | 6.20 | 5.75 |
| 2.2 | Allyl | 5.53 | 5.25 |
| 2.3 | —CH$_2$—C(=O)—O-ethyl | 6.57 | 6.05 |
| 2.4 | 2-hydroxyethyl | 4.27 | 3.97 |
| 2.5 | —CH$_2$—C(=O)—O-methyl | 6.09 | 5.66 |
| 2.6 | but-2-en-1-yl | 6.11 | 5.66 |

TABLE 2-continued
Compounds of the formula (I) in which R₁ is sec-butyl (B1a) or isopropyl (B1b) and R₂ is methyl:
| No. | R₃ | Retention time (min) B1a | B1b |
|---|---|---|---|
| 2.7 | 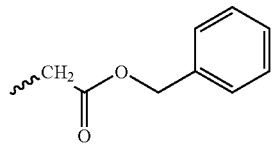 | 7.53 | 7.08 |
| 2.8 | —CH₂—C(=O)—O-t-butyl | 7.05 | 6.59 |
| 2.9 | (4-fluoro-2-trifluoromethylphenyl)methyl | 9.49 | 8.97 |
| 2.10 | (4-fluoro-3-trifluoromethylphenyl)methyl | 7.25 | 6.61 |
| 2.11 | (3,4-difluorophenyl)methyl | 6.55 | 6.11 |
| 2.12 | Isopropyl | 4.48 | 4.13 |
| 2.13 | (3-trifluoromethylphenyl)methyl | 7.38 | 6.96 |
| 2.14 | 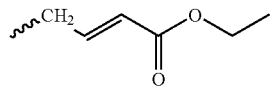 | 6.40 | 5.99 |
| 2.15 | 2-methylallyl | 6.19 | 5.88 |
| 2.16 | —CH₂—C(=O)—OH | 6.42 | 5.91 |
| 2.17 | —CH₂—C(=O)—NH₂ | 5.27 | 4.97 |
| 2.18 | 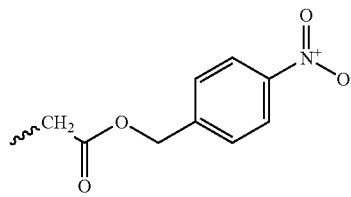 | 8.18 | 7.69 |
| 2.19 | (2-methylphenyl)methyl | 7.02 | 6.59 |
| 2.20 | 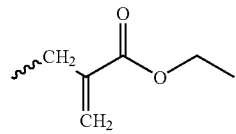 | 6.55 | 6.15 |
| 2.21 | 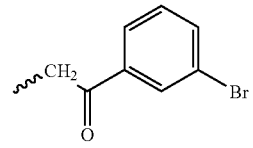 | 5.20 | 5.00 |
| 2.22 | Ethyl | 5.11 | 4.67 |
| 2.23 | 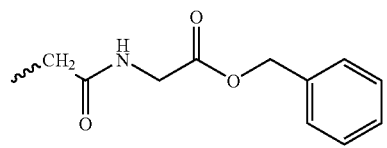 | 7.08 | 6.62 |
| 2.24 | 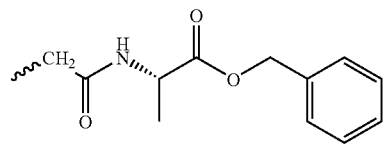 | 6.95 | 6.55 |

TABLE 2-continued

Compounds of the formula (I) in which R₁ is sec-butyl (B1a) or isopropyl (B1b) and R₂ is methyl:

| No. | R₃ | Retention time (min) B1a | B1b |
|---|---|---|---|
| 2.25 | -CH₂-C(CH₃)₂-OH | 4.98 | 4.55 |
| 2.26 | (4-phenylphenyl)methyl | 7.84 | 7.43 |
| 2.27 | -CH₂-CH=CH-C≡C-C(CH₃)₃ (cis) | 7.86 | 7.59 |
| 2.28 | -CH₂-CH=CH-C≡C-C(CH₃)₃ (trans) | 6.56 | 6.12 |
| 2.29 | (4-t-butylphenyl)methyl | 8.32 | 7.94 |
| 2.30 | (4-fluorophenyl)methyl | 6.88 | 6.49 |
| 2.31 | (4-bromophenyl)methyl | 7.50 | 7.07 |
| 2.32 | 2-bromoallyl | | |
| 2.33 | —CH₂—C(=O)—O-i-propyl | | |
| 2.34 | —CH₂—C(=O)—O—CH₂—CH₂—O—CH₃ | | |
| 2.35 | (2,3,4-trifluorophenyl)methyl | | |
| 2.36 | (2,4,5-trifluorophenyl)methyl | | |
| 2.37 | (2,3,6-trifluorophenyl)methyl | | |
| 2.38 | (3,5-dibromophenyl)methyl | | |
| 2.39 | (3-fluoro-6-bromophenyl)methyl | | |
| 2.40 | (2,3-dichlorophenyl)methyl | | |
| 2.41 | (2,6-dichlorophenyl)methyl | | |
| 2.42 | (2,5-dichlorophenyl)methyl | | |
| 2.43 | (3,4-dichlorophenyl)methyl | | |
| 2.44 | (2-fluoro-3-chlorophenyl)methyl | | |
| 2.45 | (2-chloro-4-fluorophenyl)methyl | | |
| 2.46 | (2,5-difluorophenyl)methyl | | |
| 2.47 | (2,6-difluorophenyl)methyl | | |
| 2.48 | (2,3-difluorophenyl)methyl | | |
| 2.49 | (3,5-difluorophenyl)methyl | | |
| 2.50 | (3-bromophenyl)methyl | | |
| 2.51 | (2-chlorophenyl)methyl | | |
| 2.52 | (2-fluorophenyl)methyl | | |
| 2.53 | (3-fluorophenyl)methyl | | |
| 2.54 | (4-iodophenyl)methyl | | |
| 2.55 | (2-iodophenyl)methyl | | |
| 2.56 | (4-nitrophenyl)methyl | | |
| 2.57 | (3-nitrophenyl)methyl | | |
| 2.58 | (2-chloro-5-[trifluoromethyl]phenyl)methyl | | |
| 2.59 | (3-fluoro-5-[trifluoromethyl]phenyl)methyl | | |
| 2.60 | (3,5-dichlorophenyl)methyl | | |
| 2.61 | (2-trifluoromethylphenyl)methyl | | |
| 2.62 | (3-trifluoromethoxyphenyl)methyl | | |
| 2.63 | (4-cyanophenyl)methyl | | |
| 2.64 | (2-cyanophenyl)methyl | | |
| 2.65 | (3-cyanophenyl)methyl | | |
| 2.66 | (2,3-dichloro-4-methoxyphenyl)methyl | | |
| 2.67 | -CH₂-C(=O)-NH-(2-chlorophenyl) | | |
| 2.68 | (4-difluoromethoxyphenyl)methyl | 7.88 | 7.56 |
| 2.69 | (2-fluoro-3-methylphenyl)methyl | | |

TABLE 2-continued

Compounds of the formula (I) in which R₁ is sec-butyl (B1a) or isopropyl (B1b) and R₂ is methyl:

| No. | R₃ | Retention time (min) B1a | B1b |
|---|---|---|---|
| 2.70 | (structure: CH₂-C(OEt)=CH-C(=O)-O-Et) | | |
| 2.71 | ([3,5-bis-trifluoromethyl]phenyl)methyl | | |
| 2.72 | ([2,4-bis-trifluoromethyl]phenyl)methyl | | |
| 2.73 | (structure: 4-(methoxycarbonyl)benzyl) | | |
| 2.74 | (structure: 3-(methoxycarbonyl)benzyl) | | |
| 2.75 | (3,5-dimethylphenyl)methyl | | |
| 2.76 | (2-methoxy-4-methoxycarobnylphenyl)methyl | | |
| 2.77 | (structure: 2-naphthylmethyl) | | |
| 2.78 | (structure: CH₂-CH=CH-C(=O)-O-CH₂-C(=O)-Ph) | 6.94 | 6.67 |
| 2.79 | (2-phenylphenyl)methyl | | |
| 2.80 | (4-phenylphenyl)methyl | | |
| 2.81 | (structure: (2'-cyanobiphenyl-4-yl)methyl) | | |
| 2.82 | n-propyl | 5.18 | 4.81 |
| 2.83 | isopropyl | | |
| 2.84 | n-butyl | 5.77 | 5.34 |
| 2.85 | n-pentyl | 5.93 | 5.55 |
| 2.86 | n-hexyl | 6.52 | 6.09 |
| 2.87 | n-heptyl | 7.10 | 6.62 |
| 2.88 | n-octyl | 7.32 | 7.00 |
| 2.89 | isobutyl | 5.66 | 5.23 |
| 2.90 | sec-butyl | | |
| 2.91 | tert-butyl | | |
| 2.92 | isopentyl | 5.98 | 5.61 |
| 2.93 | neopentyl | 5.99 | 5.49 |
| 2.94 | isohexyl | | |

TABLE 2-continued

Compounds of the formula (I) in which $R_1$ is sec-butyl (B1a) or isopropyl (B1b) and $R_2$ is methyl:

| No. | $R_3$ | Retention time (min) B1a | B1b |
|---|---|---|---|
| 2.95 | (CH2-NH-C(=O)-CH(CH3)-COOH structure) | 5.61 | 5.18 |
| 2.96 | (meta-methylbenzoate structure) | | |
| 2.97 | trifluoromethyl | 10.60 | |
| 2.98 | propargyl | 6.63 | 6.25 |
| 2.99 | (dibenzyl glutamate amide structure) | 8.54 | |
| 2.100 | 3,3-dichloroallyl | 5.99 | 5.61 |
| 2.101 | 2-chloroallyl | 7.63 | 7.04 |
| 2.102 | 3,3,3-trifluoropropyl | 6.14 | 5.66 |
| 2.103 | (O-benzyl tyrosine benzyl ester amide structure) | 9.34 | |
| 2.104 | (phenylalanine benzyl ester amide structure) | 8.41 | |
| 2.105 | 3-hydroxypropyl | 4.70 | 4.38 |
| 2.106 | n-nonyl | 7.74 | 7.42 |
| 2.107 | n-decyl | 8.38 | 8.06 |
| 2.108 | 3-iodopropyl | 5.12 | 4.75 |
| 2.109 | cyclobutyl | 5.50 | 5.13 |
| 2.110 | —(CH$_2$)$_3$N(CH$_3$)$_2$ | 3.41 | 3.04 |
| 2.111 | —(CH$_2$)$_3$NH$_2$ | 3.29 | |
| 2.112 | —(CH$_2$)$_3$NHCH$_3$ | 3.37 | |
| 2.113 | (propyl acetate structure) | 4.77 | 4.38 |

TABLE 2-continued
Compounds of the formula (I) in which R₁ is sec-butyl (B1a) or isopropyl (B1b) and R₂ is methyl:
| No. | R₃ | Retention time (min) B1a | B1b |
|---|---|---|---|
| 2.114 | 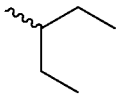 | 5.58 | 5.09 |
| 2.115 | —CH₂—CH=CH—CH₂—Cl | 5.71 | 5.29 |
| 2.116 | —CH₂—CH=CH—CH₂—N(CH₃)₂ | 3.26 | 3.07 |
| 2.117 | 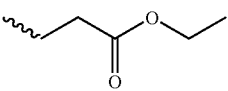 | 5.60 | 5.28 |
| 2.118 | —CH₂—CH₂—CN | 5.66 | 5.28 |
| 2.119 | 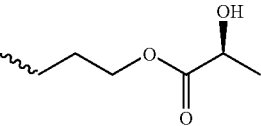 | | |
| 2.120 | 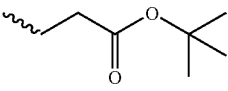 | 6.29 | 5.92 |
| 2.121 |  | 5.74 | 5.39 |
| 2.122 | —CH₂—CN | 10.23 | |
| 2.123 | 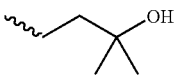 | 5.33 | 5.02 |
| 2.124 | 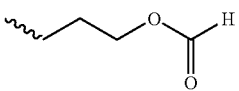 | 5.07 | 4.76 |
| 2.125 | 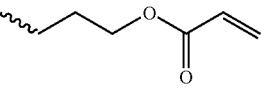 | 5.24 | 5.01 |
| 2.126 | 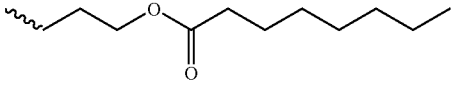 | 7.74 | 7.47 |
| 2.127 | 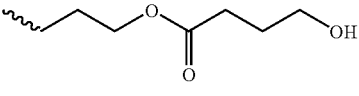 | 4.70 | 4.43 |
| 2.128 | 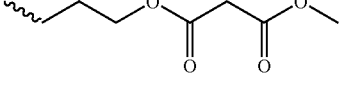 | 5.17 | 4.87 |
| 2.129 | 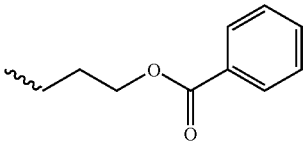 | 6.17 | 5.88 |

TABLE 2-continued
Compounds of the formula (I) in which R₁ is sec-butyl (B1a) or isopropyl (B1b) and R₂ is methyl:
| No. | R₃ | Retention time (min) B1a | B1b |
|---|---|---|---|
| 2.130 | 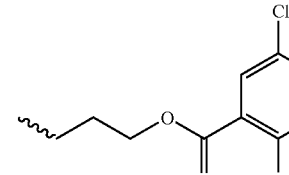 | 6.88 | 6.51 |
| 2.131 | 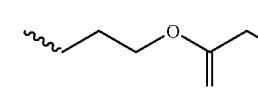 | 5.60 | 5.28 |
| 2.132 | 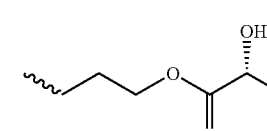 | 4.75 | 4.46 |
| 2.133 | 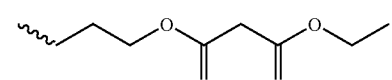 | 5.59 | |
| 2.134 | 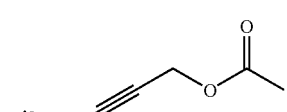 | 5.39 | 5.01 |
| 2.135 | 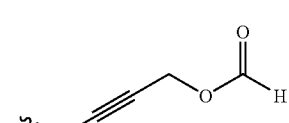 | 5.33 | 4.91 |
| 2.136 | 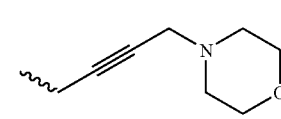 | 3.83 | 3.63 |
| 2.137 | 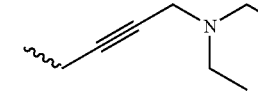 | 4.08 | 3.78 |
| 2.138 |  | 4.77 | 4.45 |
| 2.139 |  | 3.80 | 3.60 |
| 2.140 |  | 7.86 | 7.37 |

TABLE 2-continued

Compounds of the formula (I) in which $R_1$ is sec-butyl (B1a) or isopropyl (B1b) and $R_2$ is methyl:

| No. | $R_3$ | Retention time (min) B1a | B1b |
|---|---|---|---|
| 2.141 | (propanoate of but-2-ynyl) | 5.81 | 5.39 |
| 2.142 | (thiomorpholinyl but-2-ynyl) | 4.91 | 4.54 |
| 2.143 | (indolinyl but-2-ynyl) | 6.36 | 5.94 |
| 2.144 | (2,4,6-trimethylbenzoate) | 7.80 | 7.35 |
| 2.145 | (ethoxyacetate) | 7.27 | 6.76 |
| 2.146 | (pyrazine-2-carboxylate) | 6.83 | 6.29 |
| 2.147 | (pent-3-enoate) | 8.22 | 7.78 |
| 2.148 | (5-bromonicotinate) | 8.11 | 7.63 |
| 2.149 | (long chain alkanoate) | 13.55 | 13.30 |
| 2.150 | (2-fluoronicotinate) | 5.37 | 5.13 |

TABLE 2-continued

Compounds of the formula (I) in which $R_1$ is sec-butyl (B1a) or isopropyl (B1b) and $R_2$ is methyl:

| No. | $R_3$ | Retention time (min) B1a | B1b |
|---|---|---|---|
| 2.151 | 4-F, 2-Cl benzoate propyl ester | 6.43 | 6.03 |
| 2.152 | methylsulfonylacetate propyl ester | 4.86 | 4.59 |
| 2.153 | methoxyacetate propyl ester | 5.01 | 4.75 |
| 2.154 | N-butyl-N-methyl-aminobutynyl | 3.81 | 3.64 |
| 2.155 | N-cyclohexyl-N-methyl-aminobutynyl | 3.91 | 3.70 |
| 2.156 | 4-methylpiperazinyl-butynyl | 3.48 | 3.31 |
| 2.157 | N-ethyl-N-methyl-aminobutynyl | 3.63 | 3.41 |
| 2.158 | N,N-dipropyl-aminobutynyl | 4.11 | 3.79 |
| 2.159 | methylsulfonylacetate butenyl ester | 5.04 | |
| 2.160 | 2-isopropyl-imidazol-1-yl-butynyl | 3.72 | |
| 2.161 | N,N-diethyl-dithiocarbamate butynyl | 4.05 | 3.84 |

TABLE 2-continued

Compounds of the formula (I) in which $R_1$ is sec-butyl (B1a) or isopropyl (B1b) and $R_2$ is methyl:

| No. | $R_3$ | Retention time (min) | |
|---|---|---|---|
| | | B1a | B1b |
| 2.162 | [structure: propargyl-S-C(=S)-N(CH₃)₂] | 3.79 | 3.42 |
| 2.163 | [structure: propargyl-S-(2-pyridyl N-oxide)] | 4.67 | 4.37 |
| 2.164 | [structure: propargyl-S-C≡N] | 5.50 | 5.11 |
| 2.165 | [structure: propyl-NH-C(=O)-CH(Et)-Et] | 5.49 | 5.17 |
| 2.166 | [structure: propyl-NH-C(=O)-CH₂-O-Et] | 4.80 | 4.48 |
| 2.167 | [structure: propyl-NH-C(=O)-CH₂CH₂-O-Me] | 4.75 | 4.53 |
| 2.168 | [structure: propyl-NH-C(=O)-phenyl] | 5.33 | 4.96 |
| 2.169 | [structure: propyl-NH-C(=O)-CH₂-O-CH₂CH₂-O-Me] | 4.64 | 4.37 |
| 2.170 | [structure: propyl-NH-C(=O)-CH=CH-CH₃] | 4.85 | 4.48 |
| 2.171 | [structure: propyl-NH-C(=O)-C(CH₃)₃] | 5.49 | 5.07 |

TABLE 2-continued

Compounds of the formula (I) in which R₁ is sec-butyl (B1a) or isopropyl (B1b) and R₂ is methyl:

| No. | R₃ | Retention time (min) B1a | B1b |
|---|---|---|---|
| 2.172 | *~~N(H)C(O)CH(CH₃)₂ propyl linker* | 4.96 | 4.64 |
| 2.173 | *~~N(H)C(O)-3-furyl propyl linker* | 4.85 | 4.59 |
| 2.174 | *~~N(H)C(O)CH₂OH propyl linker* | 4.37 | 4.11 |
| 2.175 | *~~N(H)C(O)CH₂CH₂CH(CH₃)₂ propyl linker* | 5.60 | 5.28 |
| 2.176 | *~~N(H)C(O)CH₂OCH₃ propyl linker* | 4.59 | 4.27 |
| 2.177 | *~~CH₂OCH₂C₆H₅* | 6.29 | 5.87 |
| 2.178 | *~~C≡C—CH₂—N(iPr)CH₂CH₂OH* | 3.52 | 3.36 |
| 2.179 | *~~S—C(=S)—N(Et)₂ propyl linker* | 6.56 | 6.08 |
| 2.180 | *~~S—C(=S)—N(Me)₂ propyl linker* | 5.81 | 5.44 |
| 2.181 | —(CH₂)₃—SCN | 5.16 | |
| 2.182 | *~~S-(pyridine N-oxide) propyl linker* | 4.69 | |
| 2.183 | —(CH₂)₂—C₆H₅ | 6.13 | 5.71 |

TABLE 2-continued
Compounds of the formula (I) in which $R_1$ is sec-butyl (B1a) or isopropyl (B1b) and $R_2$ is methyl:
| No. | $R_3$ | Retention time (min) B1a | B1b |
|---|---|---|---|
| 2.184 | 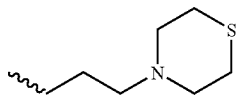 | 3.52 | 3.36 |
| 2.185 | 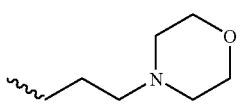 | 3.58 | 3.36 |
| 2.186 | —(CH$_2$)$_3$—C$_6$H$_5$ | 6.40 | 5.92 |
| 2.187 | 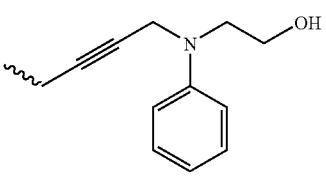 | 5.55 | 5.17 |
| 2.188 | 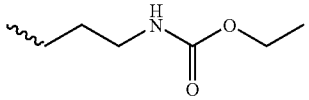 | 5.23 | 4.96 |
| 2.189 | 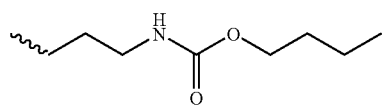 | 5.87 | 5.55 |
| 2.190 | 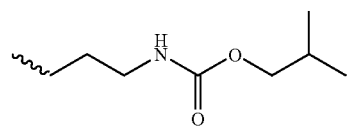 | 6.03 | 5.65 |
| 2.191 | 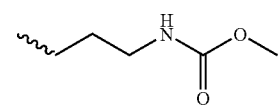 | 4.91 | 4.64 |
| 2.192 | 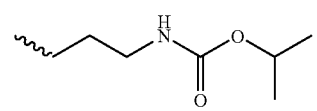 | 5.44 | 5.12 |
| 2.193 | 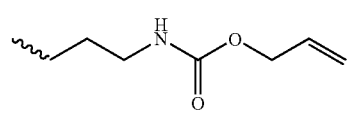 | 5.55 | 5.23 |
| 2.194 | 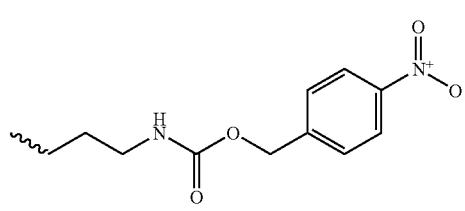 | 5.71 | 5.44 |

TABLE 2-continued

Compounds of the formula (I) in which $R_1$ is sec-butyl (B1a) or isopropyl (B1b) and $R_2$ is methyl:

| No. | R₃ | Retention time (min) B1a | B1b |
|---|---|---|---|
| 2.195 | [structure: propyl-NH-C(=O)-O-octyl carbamate] | 7.69 | 7.36 |
| 2.196 | [structure: propyl-NH-C(=O)-O-CH₂CH₂CH=CH₂ carbamate] | 5.60 | 5.28 |
| 2.197 | [structure: propyl-NH-C(=O)-O-propyl carbamate] | 5.71 | 5.33 |
| 2.198 | [structure: propyl-NH-C(=O)-CH₃ acetamide] | 4.48 | 4.21 |
| 2.199 | [structure: propyl-NH-SO₂-butyl] | 5.28 | 4.96 |
| 2.200 | [structure: propyl-NH-SO₂-ethyl] | 4.80 | 4.53 |
| 2.201 | [structure: propyl-NH-SO₂-isopropyl] | 5.07 | 4.80 |
| 2.202 | [structure: propyl-NH-SO₂-(4-Cl-phenyl)] | 5.81 | 5.49 |
| 2.203 | [structure: propyl-NH-SO₂-CH₂-phenyl] | 5.63 | 5.31 |
| 2.204 | [structure: propyl-NH-SO₂-(4-F-phenyl)] | 5.82 | 5.44 |
| 2.205 | [structure: propyl-NH-SO₂-(4-OMe-phenyl)] | 5.71 | 5.44 |

TABLE 2-continued
Compounds of the formula (I) in which R₁ is sec-butyl (B1a) or isopropyl (B1b) and R₂ is methyl:
| No. | R₃ | Retention time (min) B1a | B1b |
|---|---|---|---|
| 2.206 | 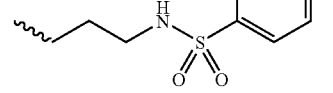 | 5.92 | 5.60 |
| 2.207 | 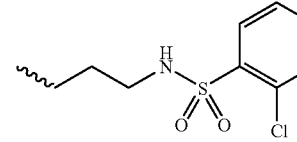 | 5.98 | 5.60 |
| 2.208 | 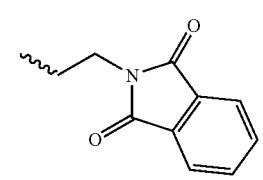 | | |
| 2.209 | —CH₂)₂NH₂ | | |
| 2.210 | —(CH₂)₂N(CH₃)₂ | | |
| 2.211 | 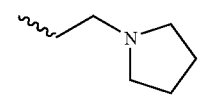 | | |
| 2.212 | 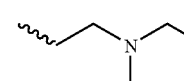 | | |
| 2.213 | 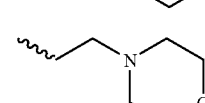 | | |
| 2.214 | 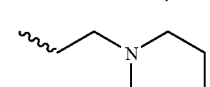 | | |
| 2.215 | 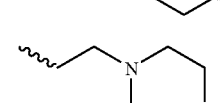 | | |
| 2.216 | 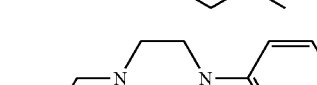 | | |
| 2.217 | 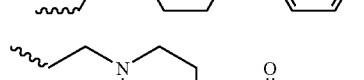 | | |
| 2.218 | 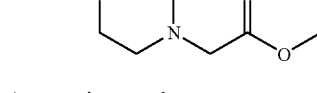 | | |

TABLE 2-continued

Compounds of the formula (I) in which $R_1$ is sec-butyl (B1a) or isopropyl (B1b) and $R_2$ is methyl:

| No. | $R_3$ | Retention time (min) B1a | B1b |
|---|---|---|---|
| 2.219 | ~CH₂CH₂-N(piperazine)N-CH₂-C(CH₃)₂-OH | | |
| 2.220 | ~CH₂CH₂-NH-C(=O)-CH₃ | | |
| 2.221 | ~CH₂CH₂-NH-C(=O)-O-CH₃ | | |
| 2.222 | ~CH₂CH₂-NH-C(=O)-CH₂-O-CH₃ | | |
| 2.223 | ~CH₂CH₂-NH-C(=O)-C₆H₅ | | |
| 2.224 | ~CH₂CH₂-NH-C(=O)-NH-C₆H₅ | | |
| 2.225 | ~CH₂CH₂-NH-S(=O)₂-CH₂CH₃ | | |
| 2.226 | ~CH₂CH₂-NH-S(=O)₂-C₆H₅ | | |
| 2.227 | —(CH₂)₄NH₂ | | |
| 2.228 | —(CH₂)₄N(CH₃)₂ | | |
| 2.229 | ~(CH₂)₃-NH-C(=O)-CH₃ | | |
| 2.230 | ~(CH₂)₃-NH-C(=O)-O-CH₃ | | |
| 2.231 | ~CH₂CH₂-O-CH₂CH₂-NH₂ | | |

TABLE 2-continued

Compounds of the formula (I) in which R₁ is sec-butyl (B1a) or isopropyl (B1b) and R₂ is methyl:

| No. | R₃ | Retention time (min) B1a | B1b |
|---|---|---|---|
| 2.232 | ~O~N(CH₃)₂ | | |
| 2.233 | ~O~NHC(O)CH₃ | | |
| 2.234 | ~O~NHC(O)OCH₃ | | |
| 2.235 | ~-phthalimide | | |
| 2.236 | ~O~-phthalimide | | |
| 2.237 | ~NHC(O)NH-(3-methylphenyl) | | |
| 2.238 | ~NHC(O)NH-(4-chlorophenyl) | | |
| 2.239 | ~NHC(O)NH-(3,4-dichlorophenyl) | | |
| 2.240 | ~NHC(O)NH-phenyl | | |
| 2.241 | ~NHC(O)NH-(1-naphthyl) | | |

TABLE 2-continued

Compounds of the formula (I) in which $R_1$ is sec-butyl (B1a) or isopropyl (B1b) and $R_2$ is methyl:

| No. | $R_3$ | Retention time (min) B1a | B1b |
|---|---|---|---|
| 2.242 | *~~N(H)-C(O)-N(H)-butyl* | | |
| 2.243 | *~~N(H)-C(O)-N(H)-(4-methoxyphenyl)* | | |
| 2.244 | *~~N(H)-C(O)-N(H)-cyclohexyl* | | |
| 2.245 | *~~N(H)-C(O)-N(H)-propyl* | | |
| 2.246 | *~~N(H)-C(O)-N(H)-(3-trifluoromethylphenyl)* | | |
| 2.247 | *~~N(H)-C(O)-N(H)-(2-chlorophenyl)* | | |
| 2.248 | *~~N(H)-C(O)-N(H)-(3-methoxyphenyl)* | | |

TABLE 3

Compounds of the formula (I) in which $R_1$ is sec-butyl (B1a) or isopropyl (B1b):

| No. | $R_2$ | $R_3$ | Retention time (min) B1a | B1b |
|---|---|---|---|---|
| 3.1 | 3-phenylallyl | 3-phenylallyl | 8.54 | 8.08 |
| 3.2 | —(CH$_2$)$_4$— | | 5.69 | 5.28 |
| 3.3 | —(CH$_2$)$_3$— | | 5.50 | 5.13 |
| 3.4 | 3-phenyl-n-propyl | 3-phenyl-n-propyl | 8.46 | 7.99 |
| 3.5 | 3,7-dimethyloct-6-en-1-yl | 3,7-dimethyloct-6-en-1-yl | 10.74 | 10.57 |

TABLE 3-continued

Compounds of the formula (I) in which $R_1$ is sec-butyl (B1a) or isopropyl (B1b):

| No. | $R_2$ | $R_3$ | Retention time (min) B1a | B1b |
|---|---|---|---|---|
| 3.6 | ethyl | —CH$_2$-(4-stilbenyl) (4-styrylbenzyl) | 8.28 | — |
| 3.7 | ethyl | ethyl | 5.73 | 5.31 |
| 3.8 | —CH$_2$CH$_2$C(CH$_3$)$_3$ | —CH$_2$CH$_2$C(CH$_3$)$_3$ | 9.11 | 8.64 |
| 3.9 | —CH$_2$CH(CH$_3$)CH$_2$CH$_2$CH$_2$C(CH$_3$)$_2$OH | —CH$_2$CH(CH$_3$)CH$_2$CH$_2$CH$_2$C(CH$_3$)$_2$OH | 8.34 | 7.85 |
| 3.10 | —CH$_2$—CH(OH)—CH$_2$— | | | 5.12 |
| 3.11 | —CH$_2$—CH$_2$—CH(OH)—CH$_2$— | | 5.53 | 5.15 |
| 3.12 | —CH$_2$CH=CH—C≡C—C(CH$_3$)$_3$ | —CH$_2$CH=CH—C≡C—C(CH$_3$)$_3$ | 10.75 | 10.36 |
| 3.13 | ethyl | benzyl | | |
| 3.14 | ethyl | allyl | 4.38 | 4.11 |
| 3.15 | ethyl | —CH$_2$C(=O)OC$_2$H$_5$ | 6.21 | 5.74 |
| 3.16 | 3-methyl-n-butyl | 3-methyl-n-butyl | | |
| 3.17 | 3-phenyl-n-butyl | 3-phenyl-n-butyl | | |
| 3.18 | ethyl | n-propyl | | |
| 3.19 | ethyl | isopropyl | | |
| 3.20 | ethyl | n-butyl | | |
| 3.21 | ethyl | pentyl | | |
| 3.22 | ethyl | hexyl | | |
| 3.23 | ethyl | heptyl | | |
| 3.24 | ethyl | n-octyl | | |
| 3.25 | ethyl | sec-butyl | | |
| 3.26 | ethyl | tert-butyl | | |
| 3.27 | ethyl | isopentyl | | |
| 3.28 | ethyl | neopentyl | | |
| 3.29 | ethyl | isohexyl | | |
| 3.30 | —(CH$_2$)$_5$— | | | |
| 3.31 | —(CH$_2$)-cyclopropyl | —(CH$_2$)—cyclopropyl | 6.13 | 5.71 |
| 3.32 | —(CH$_2$)$_2$—O—(CH$_2$)$_2$— | | | |
| 3.33 | —(CH$_2$)$_2$—S—(CH$_2$)$_2$— | | | |
| 3.34 | —(CH$_2$)$_2$—NH—(CH$_2$)$_2$— | | | |
| 3.35 | —(CH$_2$)$_2$—NCH$_3$—(CH$_2$)$_2$— | | | |
| 3.36 | —(CH$_2$)$_2$—N(i-Propyl)—(CH$_2$)$_2$— | | | |
| 3.37 | —(CH$_2$)$_2$—N(CH$_2$CH$_2$OH)—(CH$_2$)$_2$— | | | |
| 3.38 | —CH$_2$CH$_2$—N(CH$_2$C(=O)OEt)—CH$_2$CH$_2$— | | | |
| 3.39 | —CH$_2$CH$_2$—N(CH$_2$C(CH$_3$)$_2$OH)—CH$_2$CH$_2$— | | | |

TABLE 3-continued

Compounds of the formula (I) in which $R_1$ is sec-butyl (B1a) or isopropyl (B1b):

| No. | $R_2$ | $R_3$ | Retention time (min) B1a | B1b |
|---|---|---|---|---|
| 3.40 | —(CH$_2$)$_2$—N(C(=O)CH$_3$)—(CH$_2$)$_2$— | | | |
| 3.41 | —(CH$_2$)$_2$—N(C$_6$H$_5$)—(CH$_2$)$_2$— | | | |
| 3.42 | —(CH$_2$)$_2$—N(CH$_2$C$_6$H$_5$)—(CH$_2$)$_2$— | | | |

Formulation examples for use in crop protection (%=per cent by weight)

Example F1

| Emulsion concentrates | a) | b) | c) |
|---|---|---|---|
| Active compound | 25% | 40% | 50% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing of finely ground active compound and additives gives an emulsion concentrate which, by dilution with water, affords emulsions of the desired concentration.

Example F2

| Solutions | a) | b) | c) | d) |
|---|---|---|---|---|
| Active compound | 80% | 10% | 5% | 95% |
| Ethylene glycol monomethyl ether | — | 20% | — | — |
| Polyethylene glycol (MW 400) | — | — | 70% | — |
| N-methylpyrrolid-2-one | 20% | — | — | — |
| Epoxidized coconut oil | — | — | — | 1% |
| Petroleum ether (boiling range: 160-190°) | — | — | 94% | — |

Mixing of finely ground active compound and additives gives a solution suitable for use in the form of microdrops.

Example F3

| Granules | a) | b) | c) | d) |
|---|---|---|---|---|
| Active compound | 5% | 10% | 8% | 21% |
| Kaolin | 94% | — | 79% | 54% |
| Finely divided silicic acid | 1% | — | 13% | 7% |
| Attapulgite | — | 90% | — | 18% |

The active compound is dissolved in dichloromethane, the solution is sprayed onto the mixture of carriers and the solvent is evaporated under reduced pressure.

Example F4

| Wettable powder | a) | b) | c) |
|---|---|---|---|
| Active compound | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Active compound and additives are mixed and the mixture is ground in a suitable mill. This gives wettable powders which can be diluted with water to give suspensions of the desired concentration.

Example F5

| Emulsion concentrate | |
|---|---|
| Active compound | 10% |
| Octylphenol polyethylene glycol ether (4-5 mol of EO) | 3% |
| Calcium dodecylbenzenesulphonate | 3% |
| Castor oil polyethylene glycol ether (36 mol of EO) | 4% |
| Cyclohexanone | 30% |
| Xylene mixture | 50% |

Mixing of finely ground active compound and additives gives an emulsion concentrate which, by dilution with water, affords emulsions of the desired concentration.

Example F6

| Extruder granules | |
|---|---|
| Active compound | 10% |
| Sodium lignosulphonate | 2% |
| Carboxymethylcellulose | 1% |
| Kaolin | 87% |

Active compound and additives are mixed, the mixture is ground, moistened with water, extruded and granulated, and the granules are dried in a stream of air.

Example 7

| Coated granules | |
|---|---|
| Active compound | 3% |
| Polyethylene glycol (MW 200) | 3% |
| Kaolin | 94% |

In a mixer, the finely ground active compound is applied uniformly to the kaolin which has been moistened with polyethylene glycol. This gives dust-free coated granules.

Example F8

| Suspension concentrate | |
|---|---|
| Active compound | 40% |
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground active compound and additives gives a suspension concentrate which, by dilution with water, affords suspensions of the desired concentration.

BIOLOGICAL EXAMPLES

Example B1 Activity Against *Spodoptera littoralis*

Young soya bean plants are sprayed with an aqueous emulsion spray liquor which comprises 12.5 ppm of active compound, and, after the spray coating has dried on, populated with 10 caterpillars of the first stage of *Spodoptera littoralis* and introduced into a plastic container. 3 days later, the reduction in the population in per cent and the reduction in the feeding damage in per cent (% activity) are determined by comparing the number of dead caterpillars and the feeding damage between the treated and the untreated plants.

In this test, the compounds of the tables show good activity. Thus, in particular the compounds 1.001, 1.002, 1.003, 1.004, 1.005, 1.006, 1.007, 1.008, 1.009, 1.010, 1.011, 1.012, 1.013, 1.014, 1.015, 1.016, 1.017, 1.018, 1.019, 1.020, 1.021, 1.022, 1.023, 1.024, 1.025, 1.026, 1.027, 1.028, 1.029, 1.030, 1.031, 1.032, 1.033, 1.034, 1.035, 1.036, 1.037, 1.038, 1.039, 1.040, 1.041, 1.042, 1.043, 1.044, 1.045, 1.046, 1.047, 1.048, 1.050, 1.051, 1.052, 1.053, 1.054, 1.055, 1.056, 1.057, 1.058, 1.059, 1.060, 1.061, 1.062, 1.063, 1.064, 1.065, 1.066, 1.067, 1.068, 1.069, 1.070, 1.071, 1.072, 1.073, 1.074, 1.075, 1.076, 1.077, 1.078, 1.079, 1.080, 1.081, 1.082, 1.083, 1.084, 1.085, 1.086, 1.087, 1.088, 1.089, 1.090, 1.091, 1.092, 1.093, 1.094, 1.095, 1.096, 1.097, 1.098, 1.099, 1.100, 1.101, 1.102, 1.103, 1.104, 1.106, 1.107, 1.109, 1.110, 1.111, 1.112, 1.113, 1.114, 1.115, 1.116, 1.117, 1.118, 1.119, 1.120, 1.121, 1.122, 1.123, 1.124, 1.125, 1.126, 1.127, 1.128, 1.129, 1.130, 1.131, 1.132, 1.133, 1.134, 1.135, 1.136, 1.137, 1.138, 1.138, 1.139, 1.140, 1.141, 1.142, 1.143, 1.144, 1.145, 1.146, 1.147, 1.148, 1.149, 1.150, 1.151, 1.152, 1.153, 1.154, 1.155, 1.156, 1.157, 1.158, 2.001, 2.002, 2.003, 2.004, 2.005, 2.006, 2.007, 2.008, 2.009, 2.010, 2.011, 2.012, 2.013, 2.014, 2.015, 2.016, 2.017, 2.018, 2.019, 2.020, 2.021, 2.022, 2.023, 2.023, 2.024, 2.025, 2.026, 2.027, 2.028, 2.029, 2.030, 2.031, 2.032, 2.033, 2.034, 2.035, 2.036, 2.037, 2.038, 2.039, 2.040, 2.041, 2.042, 2.043, 2.044, 2.045, 2.046, 2.047, 2.048, 2.049, 2.050, 2.051, 2.052, 2.053, 2.054, 2.055, 2.056, 2.057, 2.058, 2.059, 2.060, 2.061, 2.062, 2.063, 2.064, 2.065, 2.066, 2.067, 2.068, 2.069, 2.070, 2.071, 2.072, 2.073, 2.074, 2.075, 2.076, 2.077, 2.078, 2.079, 2.080, 2.081, 3.001, 3.002, 3.003, 3.004, 3.005, 3.006, 3.007, 3.008, 3.009, 3.010, 3.011 and 3.012 effect a reduction in the pest population by more than 80%.

Example B2 Activity against *Spodoptera littoralis*, Systemic

Maize seedlings are placed into the test solution. After 6 days, the leaves are cut off, placed onto moist filter paper in a Petri dish and populated with 12 to 15 *Spodoptera littoralis* larvae of the $L_1$ stage. 4 days later, the reduction of the population in per cent (% activity) is determined by comparing the number of dead caterpillars between the treated and the untreated plants.

In this test, the compounds of the tables show good activity. Thus, in particular the compounds 1.001, 1.002, 1.003, 1.004, 1.005, 1.006, 1.007, 1.008, 1.009, 1.010, 1.012, 1.013, 1.014, 1.015, 1.016, 1.017, 1.018, 1.019, 1.020, 1.021, 1.022, 1.023, 1.024, 1.025, 1.026, 1.027, 1.028, 1.029, 1.030, 1.031, 1.032, 1.033, 1.034, 1.035, 1.036, 1.037, 1.038, 1.039, 1.040, 1.041, 1.042, 1.043, 1.044, 1.045, 1.046, 1.047, 1.048, 1.049, 1.050, 1.051, 1.052, 1.053, 1.054, 1.055, 1.056, 1.057, 1.058, 1.059, 1.060, 1.061, 1.062, 1.064, 1.065, 1.066, 1.067, 1.068, 1.069, 1.070, 1.071, 1.072, 1.073, 1.074, 1.075, 1.076, 1.077, 1.078, 1.079, 1.080, 1.081, 1.082, 1.083, 1.084, 1.085, 1.086, 1.087, 1.088, 1.089, 1.090, 1.091, 1.092, 1.093, 1.094, 1.095, 1.096, 1.097, 1.098, 1.099, 1.100, 1.101, 1.102, 1.103, 1.104, 1.105, 1.106, 1.107, 1.108, 1.109, 1.110, 1.111, 1.112, 1.113, 1.114, 1.115, 1.116, 1.117, 1.118, 1.119, 1.120, 1.121, 1.122, 1.123, 1.124, 1.125, 1.126, 1.127, 1.128, 1.129, 1.130, 1.131, 1.132, 1.133, 1.134, 1.135, 1.136, 1.137, 1.138, 1.138, 1.139, 1.140, 1.141, 1.142, 1.143, 1.144, 1.145, 1.146, 1.147, 1.148, 1.149, 1.150, 1.151, 1.152, 1.153, 1.154, 1.155, 1.156, 1.157, 1.158, 2.001, 2.002, 2.003, 2.004, 2.005, 2.006, 2.007, 2.008, 2.009, 2.010, 2.011, 2.012, 2.013, 2.014, 2.015, 2.016, 2.017, 2.018, 2.019, 2.020, 2.021, 2.022, 2.023, 2.024, 2.025, 2.026, 2.027, 2.028, 2.029, 2.030, 2.031, 2.032, 2.033, 2.034, 2.035, 2.036, 2.037, 2.038, 2.039, 2.040, 2.041, 2.042, 2.043, 2.044, 2.045, 2.046, 2.047, 2.048, 2.049, 2.050, 2.051, 2.052, 2.053, 2.054, 2.055, 2.056, 2.057, 2.058, 2.059, 2.060, 2.061, 2.062, 2.063, 2.064, 2.065, 2.066, 2.067, 2.068, 2.069, 2.070, 2.071, 2.072, 2.073, 2.074, 2.075, 2.076, 2.077, 2.078, 2.079, 2.080, 2.081, 3.001, 3.002, 3.003, 3.004, 3.005, 3.006, 3.007, 3.008, 3.009, 3.010, 3.011 and 3.012 effect a reduction in the pest population by more than 80%.

Example B3 Activity Against *Heliothis virescens*

30-35 0- to 24-hour-old eggs of *Heliothis virescens* are placed onto filter paper in a Petri dish on a layer of synthetic feed. 0.8 ml of the test solution is then pipetted onto the filter papers. Evaluation is carried out after 6 days. The reduction in the population in per cent (% activity) is determined by comparing the number of dead eggs and larvae on the treated and the untreated filter papers.

In this test, the compounds of the tables show good activity. Thus, in particular the compounds 1.001, 1.002, 1.003, 1.004, 1.005, 1.006, 1.007, 1.008, 1.009, 1.010, 1.011, 1.012, 1.013, 1.014, 1.015, 1.016, 1.017, 1.018, 1.019, 1.020, 1.021, 1.022, 1.023, 1.024, 1.025, 1.026, 1.027, 1.028, 1.029, 1.030, 1.031, 1.032, 1.033, 1.034, 1.035, 1.036, 1.037, 1.038, 1.039, 1.040, 1.041, 1.042, 1.043, 1.044, 1.045, 1.046, 1.047, 1.048, 1.052, 1.053, 1.054, 1.055, 1.056, 1.057, 1.069, 1.070, 1.071, 1.072, 1.073, 1.074, 1.075, 1.076, 1.078, 1.079, 1.080, 1.081, 1.082, 1.083, 1.084, 1.085, 1.086, 1.087, 1.088, 1.089, 1.090, 1.091, 1.092, 1.093, 1.094, 1.095, 1.096, 1.097, 1.098, 1.099, 1.100, 1.101, 1.102, 1.103, 1.104, 1.107, 1.109, 1.110, 1.111, 1.112, 1.113, 1.114, 1.115, 1.116, 1.117, 1.118, 1.119, 1.120, 1.121, 1.122, 1.123, 1.124, 1.125, 1.126, 1.127, 1.128, 1.129, 1.130, 1.131, 1.132, 1.133, 1.134, 1.135, 1.136, 1.137, 1.138, 1.138, 1.139, 1.140, 1.141, 1.142, 1.143, 1.144, 1.145, 1.147, 1.148, 1.149, 1.150, 1.151, 1.152, 1.153, 1.154, 1.155, 1.156, 1.157, 1.158, 2.001, 2.002, 2.003, 2.005, 2.006, 2.007, 2.008, 2.009, 2.010, 2.011, 2.012, 2.013, 2.014, 2.015, 2.016, 2.017, 2.018, 2.019, 2.020, 2.021, 2.026, 2.027, 2.028, 2.029, 2.030, 2.031, 2.032, 2.033, 2.034, 2.035, 2.036, 2.037, 2.038, 2.039, 2.040, 2.042, 2.043, 2.044, 2.045, 2.046, 2.047, 2.048, 2.049, 2.050, 2.051, 2.052, 2.053, 2.054, 2.055, 2.056, 2.057, 2.058, 2.059, 2.062, 2.063, 2.064, 2.066, 2.067, 2.068, 2.069, 2.070, 2.071, 2.073, 2.074, 2.075, 2.076, 2.077, 2.078, 2.079, 2.080, 2.081, 3.001, 3.002, 3.003, 3.004, 3.005, 3.006, 3.007, 3.008, 3.009 and 3.010 effect a reduction in the pest population by more than 80%.

Example B4 Activity Against *Plutella xylostella* Caterpillars

Young cabbage plants are sprayed with an aqueous emulsion spray liquor which comprises 12.5 ppm of the active compound. After the spray coating has dried on, the cabbage plants are populated with 10 caterpillars of the first stage of *Plutella xylostella* and introduced into a plastic container. Evaluation is carried out after 3 days. The reduction in the population in per cent and the reduction in the feeding damage in per cent (% activity) are determined by comparing the number of dead caterpillars and the feeding damage on the treated and the untreated plants.

In this test, the compounds of the tables show good activity against *Plutella xylostella*. Thus, in particular the compounds 1.001, 1.002, 1.003, 1.004, 1.005, 1.006, 1.007, 1.008, 1.009, 1.010, 1.011, 1.012, 1.013, 1.014, 1.015, 1.016, 1.017, 1.018, 1.019, 1.020, 1.021, 1.022, 1.023, 1.024, 1.025, 1.026, 1.027, 1.028, 1.029, 1.030, 1.031, 1.032, 1.033, 1.034, 1.035, 1.037, 1.038, 1.039, 1.040, 1.041, 1.042, 1.043, 1.046, 1.050, 1.051, 1.052, 1.053, 1.054, 1.055, 1.056, 1.057, 1.058, 1.060, 1.061, 1.070, 1.075, 1.082, 1.083, 1.084, 1.085, 1.086, 1.087, 1.088, 1.089, 1.090, 1.091, 1.092, 1.093, 1.094, 1.095, 1.096, 1.097, 1.098, 1.099, 1.100, 1.101, 1.102, 1.104, 1.113, 1.114, 1.115, 1.116, 1.117, 1.118, 1.119, 1.120, 1.121, 1.122, 1.123, 1.125, 1.126, 1.127, 1.128, 1.129, 1.130, 1.131, 1.132, 1.133, 1.134, 1.135, 1.138, 1.140, 1.141, 1.142, 1.143, 1.144, 1.145, 1.147, 1.149, 1.151, 1.152, 1.153, 1.154, 1.155, 1.156, 1.157, 1.158, 2.001, 2.002, 2.003, 2.005, 2.006, 2.007, 2.008, 2.009, 2.010, 2.011, 2.012, 2.013, 2.014, 2.015, 2.017, 2.018, 2.019, 2.020, 2.021, 2.022, 2.026, 2.027, 2.028, 2.029, 2.030, 2.031, 2.032, 2.033, 2.034, 2.035, 2.042, 2.046, 2.057, 2.068, 2.070, 2.073, 2.077, 2.078, 3.001, 3.002, 3.003, 3.004, 3.005, 3.006, 3.007, 3.008 and 3.009 effect a reduction in the pest population by more than 80%.

Example B5 Activity Against *Frankliniella occidentalis*

In Petri dishes, discs of the leaves of beans are placed onto agar and sprayed with test solution in a spraying chamber. The leaves are then populated with a mixed population of *Frankliniella occidentalis*. Evaluation is carried out after 10 days. The reduction in per cent (% activity) is determined by comparing the population on the treated leaves with that of the untreated leaves.

In particular the compounds 1.027, 1.037, 1.038, 1.039, 1.040, 1.050, 1.061, 1.065, 1.068, 1.082, 2.005, 2.006, 2.007, 2.008, 2.009, 2.010, 2.011, 2.012, 2.013, 2.014, 2.015, 2.016, 2.017, 2.018, 2.020, 2.021, 2.026, 2.027, 2.028, 2.029, 2.030, 2.032, 2.033, 2.034, 2.036, 2.038, 2.040, 2.042, 2.046, 2.047, 2.049, 2.050, 2.051, 2.055, 2.057, 2.062, 2.070, 2.071, 2.072, 3.003, 3.006 and 3.012 effect a reduction in the pest population by more than 80%.

Example B6 Activity Against *Diabrotica balteata*

Maize seedlings are sprayed with an aqueous emulsion spray liquor which comprises 12.5 ppm of active compound and, after the spray coating has dried on, populated with 10 larvae of the second stage of *Diabrotica balteata* and then introduced into a plastic container. After 6 days, the reduction in the population in per cent (% activity) is determined by comparing the dead larvae between the treated and the untreated plants.

In this test, the compounds of the tables show good activity. Thus, in particular the compounds 1.002, 1.003, 1.004, 1.005, 1.006, 1.007, 1.008, 1.009, 1.010, 1.011, 1.012, 1.013, 1.014, 1.015, 1.016, 1.017, 1.018, 1.019, 1.020, 1.021, 1.022, 1.023, 1.024, 1.025, 1.027, 1.028, 1.029, 1.030, 1.031, 1.032, 1.033, 1.034, 1.035, 1.037, 1.038, 1.039, 1.040, 1.041, 1.042, 1.043, 1.045, 1.046, 1.047, 1.048, 1.052, 1.053, 1.054, 1.055, 1.056, 1.057, 1.058, 1.059, 1.063, 1.064, 1.065, 1.066, 1.067, 1.068, 1.069, 1.070, 1.071, 1.072, 1.074, 1.075, 1.076, 1.077, 1.078, 1.079, 1.080, 1.081, 1.082, 1.083, 1.084, 1.085, 1.086, 1.087, 1.088, 1.090, 1.091, 1.092, 1.093, 1.094, 1.095, 1.096, 1.097, 1.098, 1.099, 1.100, 1.101, 1.102, 1.104, 1.105, 1.107, 1.108, 1.109, 1.111, 1.113, 1.114, 1.115, 1.116, 1.117, 1.118, 1.119, 1.120, 1.121, 1.122, 1.123, 1.125, 1.126, 1.127, 1.128, 1.129, 1.130, 1.131, 1.132, 1.133, 1.134, 1.135, 1.136, 1.137, 1.138, 1.139, 1.140, 1.141, 1.142, 1.143, 1.144, 1.145, 1.147, 1.148, 1.149, 1.150, 1.151, 1.152, 1.153, 1.154, 1.155, 1.156, 1.157, 1.158, 2.001, 2.002, 2.003, 2.004, 2.005, 2.006, 2.007, 2.008, 2.009, 2.010, 2.011, 2.012, 2.013, 2.014, 2.015, 2.016, 2.017, 2.018, 2.019, 2.020, 2.021, 2.022, 2.025, 2.026, 2.027, 2.028, 2.030, 2.031, 2.032, 2.033, 2.034, 2.046, 2.050, 2.051, 2.052, 2.056, 2.073, 2.074, 2.076, 2.077, 3.001, 3.002, 3.004, 3.005, 3.006, 3.007, 3.008 and 3.009 effect a reduction in the pest population by more than 80%.

Example B7 Activity Against *Tetranychus urticae*

Young bean plants are populated with a mixed population of *Tetranychus urticae* and, after 1 day, sprayed with an aqueous emulsion spray liquor which comprises 12.5 ppm of active compound, incubated at 25° C. for 6 days and then evaluated. The reduction in the population in per cent (% activity) is determined by comparing the number of dead eggs, larvae and adults on the treated and on the untreated plants.

In this test, the compounds of the tables show good activity. Thus, in particular the compounds 1.001, 1.002, 1.003, 1.004, 1.005, 1.006, 1.007, 1.008, 1.009, 1.010, 1.011, 1.012, 1.013, 1.014, 1.015, 1.016, 1.017, 1.018, 1.019, 1.020, 1.021, 1.022, 1.023, 1.024, 1.025, 1.026, 1.027, 1.028, 1.029, 1.030, 1.031, 1.032, 1.033, 1.034, 1.035, 1.036, 1.037, 1.038, 1.039, 1.040, 1.041, 1.042, 1.043, 1.044, 1.045 1.046, 1.047, 1.048, 1.049, 1.050, 1.051, 1.052, 1.053, 1.054, 1.055, 1.056, 1.057, 1.058, 1.059, 1.060, 1.061, 1.062, 1.063, 1.064, 1.065, 1.066, 1.067, 1.068, 1.069, 1.070, 1.071, 1.072, 1.073, 1.074, 1.075, 1.076, 1.077, 1.078, 1.079, 1.080, 1.081, 1.082, 1.083, 1.084, 1.085, 1.086, 1.087, 1.088, 1.089, 1.090, 1.091, 1.092, 1.093, 1.094, 1.095, 1.096, 1.097, 1.098, 1.099, 1.100, 1.101, 1.102, 1.103, 1.104, 1.105, 1.106, 1.107, 1.108, 1.109, 1.110, 1.111, 1.112, 1.113, 1.114, 1.115, 1.116, 1.117, 1.118, 1.119, 1.120, 1.121, 1.122, 1.123, 1.124, 1.126, 1.127, 1.128, 1.129, 1.130, 1.131, 1.132, 1.133, 1.134, 1.135, 1.136, 1.137, 1.138, 1.139, 1.140, 1.141, 1.142, 1.143, 1.144, 1.145, 1.146, 1.147, 1.148, 1.149, 1.150, 1.151, 1.152, 1.153, 1.154, 1.155, 1.156, 1.157, 1.158, 2.001, 2.002, 2.003, 2.004, 2.005, 2.006, 2.007, 2.008, 2.009, 2.010, 2.011, 2.012, 2.013, 2.014, 2.015, 2.016, 2.017, 2.018, 2.019, 2.020, 2.021, 2.022, 2.023, 2.024, 2.025, 2.026, 2.027, 2.028, 2.029, 2.030, 2.031, 2.032, 2.033, 2.034, 2.035, 2.036, 2.037, 2.038, 2.039, 2.040, 2.041, 2.042, 2.043, 2.044, 2.045, 2.046, 2.047, 2.048, 2.049, 2.051, 2.052, 2.053, 2.054, 2.055, 2.056, 2.057, 2.058, 2.059, 2.060, 2.061, 2.062, 2.063, 2.064, 2.065, 2.066, 2.067, 2.068, 2.069, 2.070, 2.071, 2.072, 2.073, 2.074, 2.075, 2.076, 2.077, 2.078, 2.079, 2.081, 3.001, 3.002, 3.003, 3.004, 3.005, 3.006, 3.007, 3.008, 3.009, 3.010, 3.011 and 3.012 effect a reduction in the pest population by more than 80%.

What is claimed is:

1. A compound of the formula

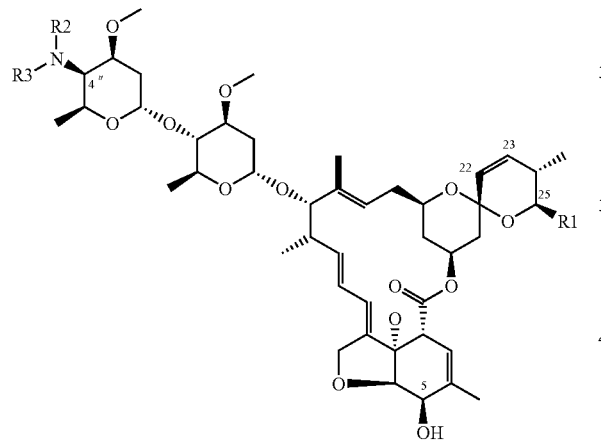

in which
$R_1$ is $C_1$-$C_{12}$alkyl, $C_3$-$C_8$cycloalkyl or $C_2$-$C_{12}$alkenyl;
$R_2$ is H, unsubstituted or mono- to pentasubstituted $C_1$-$C_{12}$alkyl or unsubstituted or mono- to pentasubstituted $C_2$-$C_{12}$alkenyl;
$R_3$ is, mono- to pentasubstituted $C_1$-$C_{12}$alkyl, unsubstituted or mono- to pentasubstituted $C_3$-$C_{12}$cycloalkyl, unsubstituted or mono- to pentasubstituted $C_1$-$C_6$alkoxy-$C_1$-$C_6$alkyl, unsubstituted or mono- to pentasubstituted $C_2C_{12}$alkenyl, unsubstituted or mono- to pentasubstituted $C_2$-$C_{12}$alkynyl; or
$R_2$ and $R_3$ together are a three- to seven-membered alkylene or a four- to seven membered alkenylene bridge, in which a $CH_2$ group may be substituted by O, S or $NR_4$;
in which the substituents of the mono- to pentasubstituted $C_1$-$C_{12}$ alkyl, mono- to pentasubstituted $C_3$-$C_{12}$cycloalkyl, mono- to pentasubstituted $C_1$-$C_6$alkoxy-$C_1$-$C_6$alkyl, mono- to pentasubstituted $C_2$-$C_{12}$alkenyl, or mono- to pentasubstituted $C_2$-$C_{12}$alkynyl groups are selected from the group consisting of OH, halogen, halo-$C_1$-$C_2$alkyl, CN, SCN, $NO_2$, $C_2$-$C_6$alkynyl, $C_3$-$C_8$-cycloalkyl which is unsubstituted or substituted by one to three methyl groups; norbornylenyl, $C_3$-$C_8$cycloalkenyl which is unsubstituted or substituted by one to three methyl groups; $C_3$-$C_8$halocycloalkyl, $C_1$-$C_{12}$alkoxy, $C_3$-$C_8$cycloalkoxy, $C_1$-$C_{12}$alkylthio, $C_3$-$C_8$cycloalkylthio, $C_1$-$C_{12}$-haloalkylthio, $C_1$-$C_{12}$alkylsulfinyl, $C_3$-$C_8$cycloalkylsulfinyl, $C_1$-$C_{12}$haloalkylsulfinyl, $C_3$-$C_8$halocycloalkylsulfinyl, $C_1$-$C_{12}$alkylsulfonyl, $C_3$-$C_8$cycloalkylsulfonyl, $C_1$-$C_{12}$haloalkylsulfonyl, $C_3$-$C_8$halocycloalkylsulfonyl, $C_2$-$C_8$alkenyl, $C_2$-$C_8$alkynyl, —$N(R_8)_2$, wherein the two $R_8$ are independent of each other; —$C(=O)R_5$, —O—$C(=O)R_6$, —$NHC(=O)R_5$, —S—$C(=S)R_6$, —$P(=O)(OC_1$-$C_6$alkyl$)_2$, —$S(=O)_2R_9$; —NH—$S(=O)_2R_9$, —OC$(=O)$—$C_1$-$C_6$alkyl-$S(=O)_2R_9$,
aryl, benzyl, heterocyclyl, aryloxy, benzyloxy, heterocyclyloxy, arylthio, benzylthio, and heterocyclylthio; wherein said aryl, heterocyclyl, aryloxy, benzyloxy, heterocyclyloxy, arylthio, benzylthio or heterocyclylthio may be unsubstituted or, depending on the possibilities of substitution on the ring, are mono- to pentasubstituted by substituents selected from the group consisting of OH, halogen, CN, $NO_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_6$alkoxy-$C_1$-$C_6$alkyl, dimethylamino-$C_1$-$C_6$alkoxy, $C_2$-$C_8$alkenyl, $C_2$-$C_8$alkynyl, phenoxy, phenyl-$C_1$-$C_6$alkyl; methylenedioxy, —$C(=O)R_5$, —O—C$(=O)$—$R_6$, —NH—$C(=O)R_6$, —$N(R_8)_2$, wherein the two $R_8$ are independent of each other; $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl and $C_3$-$C_8$halocycloalkylsulfonyl;
$R_4$ is H, $C_1$-$C_8$alkyl, hydroxy-$C_1$-$C_8$alkyl, $C_3$-$C_8$cycloalkyl, $C_2$-$C_8$alkenyl, $C_2$-$C_8$alkynyl, phenyl, benzyl, —$C(=O)R_5$, or —$CH_2$—$C(=O)$—$R_5$;
$R_5$ is H, OH, SH, —$N(R_8)_2$, wherein the two $R_8$ are independent of each other; $C_2$-$C_{12}$alkenyl, $C_1$-$C_8$hydroxyalkyl, $C_1$-$C_{12}$haloalkyl, $C_1$-$C_{12}$alkoxy, $C_1$-$C_{12}$-haloalkoxy, $C_1$-$C_6$alkoxy-$C_1$-$C_6$alkyl, $C_1$-$C_6$alkoxy-$C_1$-$C_6$alkoxy, $C_1$-$C_6$alkoxy-$C_1$-$C_6$alkoxy-$C_1$-$C_6$alkyl, $C_1$-$C_{12}$alkylthio, $C_2$-$C_8$alkenyloxy, $C_2$-$C_8$alkynyloxy, NH—$C_1$-$C_6$alkyl-$C(=O)R_7$, —N($C_1$-$C_6$alkyl)-$C_1$-$C_6$alkyl-$C(=O)$—$R_7$, —O—$C_1$-$C_2$alkyl-$C(=O)R_7$, —$C_1$-$C_6$alkyl-$S(=O)_2R_9$; aryl, benzyl, heterocyclyl, aryloxy, benzyloxy, heterocyclyloxy; or aryl, benzyl, heterocyclyl, aryloxy, benzyloxy or heterocyclyloxy, which are unsubstituted or mono- to trisubstituted in the ring independently of one another by halogen, nitro, $C_1$-$C_6$alkyl, $C_1$-$C_6$alkoxy, $C_1$-$C_6$haloalkyl or $C_1$-$C_6$haloalkoxy;
$R_6$ is H, $C_1$-$C_{24}$alkyl, $C_1$-$C_{12}$haloalkyl, $C_1$-$C_{12}$hydroxyalkyl, $C_2$-$C_8$alkenyl, $C_2$-$C_8$alkynyl, $C_1$-$C_6$alkoxy-$C_1$-$C_6$alkyl, $(NR_8)_2$, wherein the two $R_8$ are independent of each other; —$C_1$-$C_6$alkyl-$C(=O)R_8$, —$C_1$-$C_6$alkyl-$S(=O)_2R_9$, aryl, benzyl, heterocyclyl; or aryl, benzyl or heterocyclyl which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;
$R_7$ is H, OH, $C_1$-$C_{24}$alkyl which is optionally subsituted with OH, or —$S(=O)_2$—$C_1$-$C_6$alkyl; $C_1$-$C_{12}$alkenyl, $C_1$-$C_{12}$alkynyl, $C_1$-$C_{12}$alkoxy, $C_1$-$C_6$alkoxy-$C_1$-$C_6$alkyl, $C_1$-$C_6$alkoxy-$C_1$-$C_6$alkoxy, $C_2$-$C_8$alkenyloxy, aryl, aryloxy, benzyloxy, heterocyclyl, heterocyclyloxy or —$N(R_8)_2$, wherein the two $R_8$ are independent of each other;

$R_8$ H, $C_1$-$C_6$alkyl, which is optionally substituted with one to five substituents selected from the group consisting of halogen, $C_1$-$C_6$alkoxy, hydroxy and cyano; $C_1$-$C_8$-cycloalkyl, aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

$R_9$ is H, $C_1$-$C_6$alkyl, which is optionally substituted with one to five substituents selected from the group consisting of halogen, $C_1$-$C_6$alkoxy, hydroxy and cyano; aryl, benzyl, heteroaryl; or aryl, benzyl or heteroaryl, which, depending on the possibilities of substitution on the ring, are mono- to trisubstituted by substituents selected from the group consisting of OH, halogen, CN, $NO_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_{12}$alkylthio and $C_1$-$C_{12}$haloalkylthio;

with the proviso that $R_1$ is not sec-butyl or isopropyl if $R_2$ is H and $R_3$ is 2-hydroxyethyl, or benzyl;

or, if appropriate, an E/Z isomer, E/Z isomer mixture and/or tautomer thereof.

2. A pesticidal composition comprising at least one compound of the formula (I) as described in claim 1 as active compound and at least one auxiliary.

3. A method for controlling pests comprising applying a composition as described in claim 2 to the pests or their habitat.

4. A process for preparing a composition as described in claim 2 which contains at least one auxiliary, wherein the active compound is mixed intimately and/or ground with the auxiliary(s).

5. A method according to claim 3 for protecting plant propagation material, wherein the propagation material or the location where the propagation material is planted is treated.

6. A method for protecting and controlling parasitic infestations in a human, livestock, a domestic animal or a pet, comprising administering an effective amount of the compound of claim 1 to the human, livestock, domestic animal or pet.

7. The method of claim 6, wherein the parasite is an endoparasite.

8. The method of claim 6, wherein the parasite is an ectoparasite.

9. The method of claim 8, wherein the ectoparasite is a flea or a tick.

10. The method of claim 7, wherein the endoparasite is a nematode or a cestode.

11. The method of claim 6, wherein the pet is a cat or a dog.

* * * * *